(12) United States Patent
Zhao et al.

(10) Patent No.: US 11,103,324 B2
(45) Date of Patent: Aug. 31, 2021

(54) MAGNETICALLY STEERABLE CONTINUUM ROBOTIC GUIDEWIRES FOR NEUROVASCULAR APPLICATIONS

(71) Applicant: Massachusetts Institute of Technology, Cambridge, MA (US)

(72) Inventors: Xuanhe Zhao, Allston, MA (US); Yoonho Kim, Cambridge, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 0 days.

(21) Appl. No.: 16/997,213

(22) Filed: Aug. 19, 2020

(65) Prior Publication Data

US 2021/0059779 A1  Mar. 4, 2021

Related U.S. Application Data

(60) Provisional application No. 62/892,571, filed on Aug. 28, 2019.

(51) Int. Cl.
| | |
|---|---|
| *A61B 34/00* | (2016.01) |
| *A61B 34/20* | (2016.01) |
| *B25J 9/16* | (2006.01) |
| *A61B 90/30* | (2016.01) |
| *A61B 18/20* | (2006.01) |
| *A61B 18/00* | (2006.01) |

(52) U.S. Cl.
CPC .............. *A61B 34/73* (2016.02); *A61B 34/20* (2016.02); *A61B 34/71* (2016.02); *B25J 9/1682* (2013.01); *A61B 18/203* (2013.01); *A61B 2018/00577* (2013.01); *A61B 2034/2061* (2016.02); *A61B 2034/731* (2016.02); *A61B 2090/306* (2016.02)

(58) Field of Classification Search
None
See application file for complete search history.

(56) References Cited

U.S. PATENT DOCUMENTS

| | | | |
|---|---|---|---|
| 7,104,056 B2 * | 9/2006 | Taya | ....................... F03G 7/065 310/307 |
| 8,206,404 B2 | 6/2012 | De La Rama et al. | |
| 8,685,000 B2 * | 4/2014 | Buckley | ............... A61B 17/221 604/530 |
| 8,827,910 B2 | 9/2014 | De La Rama et al. | |

(Continued)

OTHER PUBLICATIONS

International Search Report and Written Opinion for PCT/US20/46928 dated Oct. 30, 2020.

(Continued)

*Primary Examiner* — Carl H Layno
*Assistant Examiner* — Manolis Pahakis
(74) *Attorney, Agent, or Firm* — Peter A. Nieves; Sheehan Phinney Bass & Green PA

(57) ABSTRACT

Robotic devices and methods for performing minimally invasive procedures on the vascular system, particularly cerebrovascular and endovascular neurosurgical procedures, where a submillimeter-scale continuum robotic device is configured and adapted for active steering and navigation based on external magnetic actuation. The submillimeter-scale continuum robotic device includes an elongate body having an inner core and an outer shell, where the outer shell is fabricated of an elastomeric material having a plurality of ferromagnetic particles dispersed therein.

40 Claims, 27 Drawing Sheets

(56) References Cited

U.S. PATENT DOCUMENTS

| | | | |
|---|---|---|---|
| 10,123,681 B2* | 11/2018 | Omoto | A61B 1/00 |
| 10,254,499 B1* | 4/2019 | Cohen | B23K 1/19 |
| 10,595,950 B2 | 3/2020 | Taya | |
| 10,743,750 B2 | 8/2020 | Hunter et al. | |
| 2002/0095169 A1* | 7/2002 | Maitland | A61B 17/320725 |
| | | | 606/194 |
| 2007/0016006 A1* | 1/2007 | Shachar | A61B 5/062 |
| | | | 600/424 |
| 2007/0260286 A1* | 11/2007 | Giftakis | A61B 5/4094 |
| | | | 607/9 |
| 2007/0270781 A1* | 11/2007 | Burgermeister | A61M 25/0105 |
| | | | 604/528 |
| 2008/0006280 A1 | 1/2008 | Aliberto et al. | |
| 2008/0021336 A1* | 1/2008 | Dobak, III | A61B 5/021 |
| | | | 600/508 |
| 2009/0312710 A1* | 12/2009 | Smith | A61B 17/3439 |
| | | | 604/164.03 |
| 2010/0305402 A1* | 12/2010 | Shachar | A61M 25/0127 |
| | | | 600/118 |
| 2011/0098769 A1* | 4/2011 | Betzold | A61N 1/36507 |
| | | | 607/25 |
| 2013/0204085 A1* | 8/2013 | Alexander | A61B 1/05 |
| | | | 600/109 |
| 2014/0121719 A1* | 5/2014 | Bonner | A61N 1/3682 |
| | | | 607/18 |
| 2014/0121720 A1* | 5/2014 | Bonner | A61N 1/3756 |
| | | | 607/18 |
| 2015/0196756 A1* | 7/2015 | Stahmann | A61N 1/37288 |
| | | | 607/4 |
| 2016/0129261 A1* | 5/2016 | Demmer | A61N 1/36585 |
| | | | 607/18 |
| 2018/0070833 A1* | 3/2018 | Chirife | A61B 5/029 |
| 2018/0140848 A1* | 5/2018 | Stahmann | A61N 1/36507 |
| 2019/0167972 A1* | 6/2019 | Stahmann | A61N 1/059 |
| 2019/0167991 A1* | 6/2019 | Stahmann | A61N 1/36514 |
| 2020/0035390 A1* | 1/2020 | Hu | H01F 1/0308 |
| 2020/0223099 A1* | 7/2020 | Kim | B29C 64/106 |
| 2020/0230361 A1* | 7/2020 | Nelson | A61M 25/0158 |

OTHER PUBLICATIONS

Shipman, "Controlling Soft Robot Movements with Light, Magnets, Control Engineering", Aug. 9, 2019.

Kim, "Printing Ferromagnetic Domains in Soft Materials: Mechanism, Modeling, and Applications"; MIT; Jun. 2018.

Zhao, "Mechanics of Hard-Magnetic Soft Materials", Journal of the Mechanics and Physics of Solids; (2019) 244-263.

Xu, "Millimeter-scale Flexible Robots with Programmable Three-Dimensional Magnetization and Motions", Science Robotics, Apr. 24, 2019.

Lum, "Shape-Programmable Magnetic Soft-Matter" PNAS, Sep. 26, 2016.

Ataka, "Magnetic-field-inspired Navigation for Soft-Continuum Manipulator", 2018 IEEE/RSJ International Conference on Intelligent Robots and Systems (IROS) Madrid, Spain, Oct. 1-5, 2018.

Schmauch et al., "Chained Iron Microparticles for Directionally Controlled Actuation of Soft Robots." ACS Appl. Mater. Interfaces201791311895-11901 (Abstract only)).

* cited by examiner

Tendon-driven   10 mm

Magnet-driven   5 mm

Cerebrovascular anatomy (artery)   10 mm

C-arm fluoroscopy (real-time imaging)

FIG. 6A
FIG. 6B
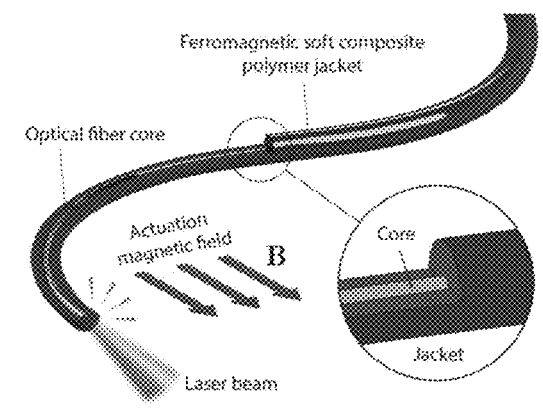
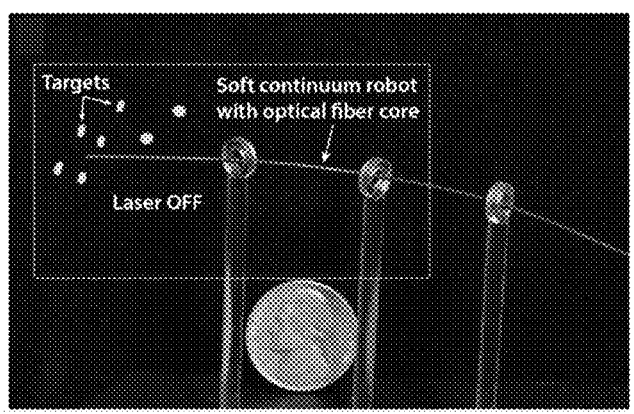
FIG. 6C
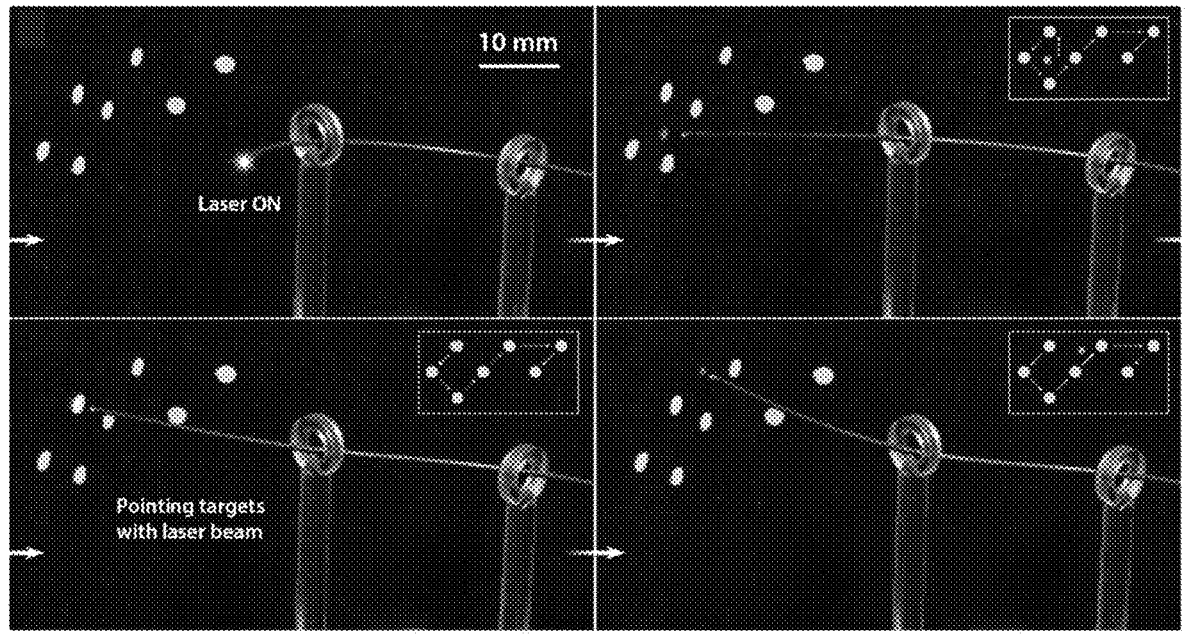

FIG. 9A
FIG. 9B
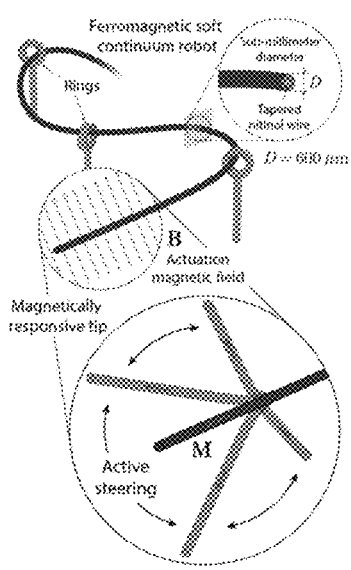
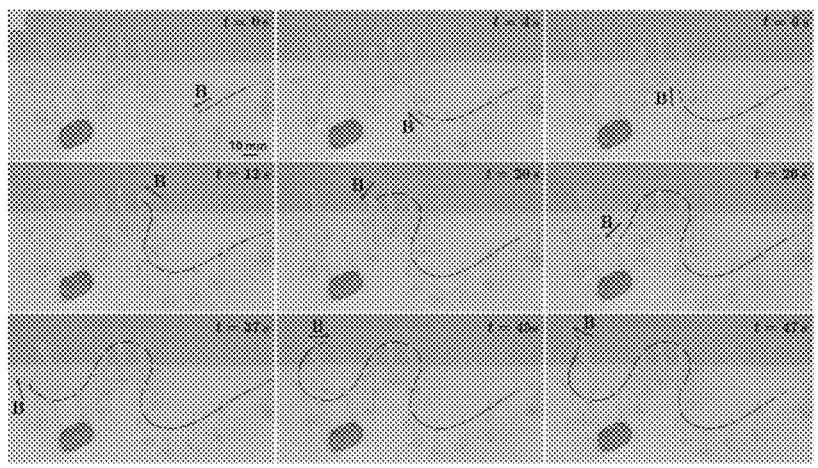

As prepared

After 10 min

After 60 min

FIG. 18A
FIG. 18B
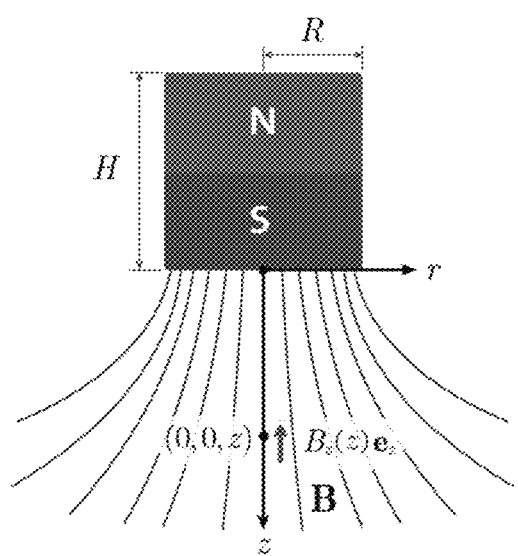
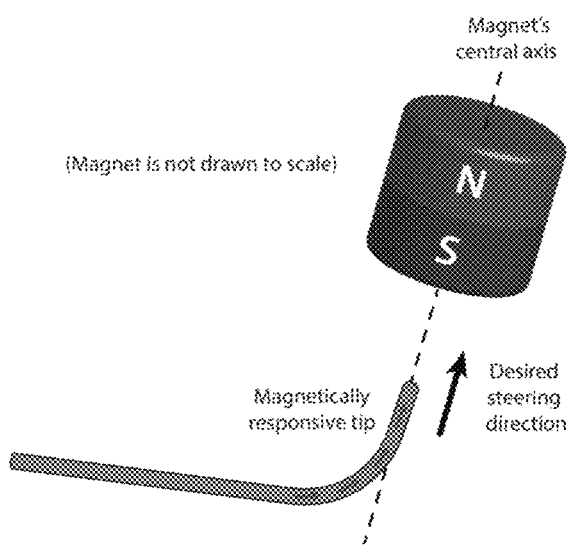

MAGNETICALLY STEERABLE CONTINUUM ROBOTIC GUIDEWIRES FOR NEUROVASCULAR APPLICATIONS

This invention was made with Government support under Grant No. N00014-17-1-2920 awarded by the Office of Naval Research, and Grant No. CMMI-1661627 awarded by the National Science Foundation. The Government has certain rights in the invention.

FIELD OF THE INVENTION

The present invention generally relates to robotic devices and methods for performing minimally invasive procedures on the vascular system, particularly cerebrovascular and endovascular neurosurgical procedures. More particularly, the present invention provides a submillimeter-scale continuum robotic device adapted for active steering and navigation based on magnetic actuation. As such, the present invention robotic device is capable of navigating the considerably smaller and more tortuous vascular structures, including the microvascular system, thereby enabling the performance of minimally invasive remote procedures on these difficult to access location.

BACKGROUND OF THE INVENTION

Stroke remains one of the main causes of death and the leading cause of long-term disabilities in the United States. Stroke kills about 140,000 Americans and costs around $34 billion each year. About 87% of all strokes result from ischemic strokes, in which blood flow to the brain is blocked by a mechanical clot (thrombus; FIG. 1A) or narrowing due to plaque buildup. The remaining 13% result from hemorrhagic strokes, which occur when a weakened blood vessel breaks, typically at an aneurysm (aneurysm; FIG. 1A), which is a localized bulge that has high risks of rupture, causing bleeding into the brain. If not treated promptly, both ischemic and hemorrhagic strokes can lead to permanent brain damage, causing serious disorders with devastating effects on the quality of life of the victims. When it comes to acute ischemic stroke, the importance of early intervention is epitomized by the well-known phrase, "time is brain", which emphasizes the fact that time is so critical when treating a stroke to achieve better protection of the brain against the irreversible damage. In general, stroke victims who are treated within 90 minutes have a substantially lower risk of permanent brain damage or death. The current treatment of acute ischemic stroke, however, still requires physically transporting patients to primary stroke centers, typically at large institutions such as university hospitals. For patients in distant or rural areas, where acute-care services are not available, the current systems of care have limitations inherent in the logistics involved.

To enable early stroke intervention, it would be beneficial to enable remote surgery through teleoperated robotic systems. Such telerobotic systems could potentially enable skilled neurosurgeons to perform required surgical tasks remotely on patients at local hospitals, obviating the need to transport the patients to large institutions at the expense of time. Despite the expected advantages, however, robotic applications to cerebrovascular and endovascular neurosurgery are lacking. The challenge of realizing miniaturized robotic devices that can navigate through the narrow and complex cerebrovascular anatomy to reach to the target lesions in a minimally invasive manner has not been met with existing technologies. While several types of robotic catheters and continuum robots have been commercialized so far, mostly for cardiac or pulmonary interventions, they are limited to large scales due to miniaturization challenges inherent in their conventional actuation mechanisms. As a result, even the most advanced form of continuum robots developed to date have remained substantially unsuited for neurosurgical applications due to considerably small and tortuous vascular structures.

In particular, in the current cerebrovascular and endovascular neurosurgery, manually controlled passive guidewires (FIGS. 1B-C), as a gold standard, remain the only means to provide access to the intracranial vasculature in a noninvasive manner. For these guidewires, the distal tip of the device is typically pre-shaped with a fixed curvature or shapeable into curved or bent shapes (FIG. 1C), instead of being straight, for steering purpose. The pre-bent distal tip can be oriented towards a desired direction by manually twisting the proximal end of the device. After orienting the tip towards a desired direction through the twisting maneuver, the proximal end is pushed to advance the whole device forward. Upon this pushing manipulation, the floppy tip conforms to the environment and passively follows the continuous path as the guidewire moves forward (FIG. 1B). However, for this passive steering method, typically multiple reshaping maneuvers are required to adjust the shape of the guidewire tip during the course of the procedure. Furthermore, this twisting-based steering method often becomes no longer effective, particularly when navigating through a highly tortuous path due to the large friction acting on the device along the path. When forced to rotate further by additional twisting, the pre-shaped tip tends to jerk, abruptly rotating excessively in an unpredictable manner. This unwanted movement substantially compromises the controllability and maneuverability.

Several concepts of continuum robots have been developed, offering safer therapeutic and diagnostic procedures owing to the minimally invasive nature. Current robotic catheters with steering and navigational capabilities can be generally categorized into two types depending on their actuation mechanisms based on: (i) passive guidewires, which can be manipulated, for example, by pulling/pushing antagonistic pairs of mechanical wires (FIG. 2A), through a steerable sheath (e.g., Magellan™ of Hansen Medical) driven by mechanical wires to steer a conventional guidewire, which can be advanced/retracted or rotated by the linear/rotary drive from the proximal end (FIGS. 2E-F), and advancing/retracting or rotating a conventional passive guidewire with a linear/rotary drive from the proximal end (e.g., Corpath® GRX of Corindus Vascular Robotics, FIG. 2H-I) or (ii) applying external magnetic fields to control rigid magnets embedded in the distal tip of the device (FIGS. 2B and 2J) and applying external magnetic fields to control a finite-sized rigid magnet attached at the distal end tip of a guidewire, where the magnet is generally thicker than the guidewire (FIG. 2G). These devices are being used in clinical settings, mostly for cardiac (e.g. to treat arrhythmia) or pulmonary (e.g. for early diagnose of lung cancer) applications by enabling minimally invasive access to the targeted lesions through arteries or lung airways. However, application of such devices to cerebrovascular and endovascular neurosurgery have remained largely unexplored due mainly to the lack of appropriate technologies. The biggest hurdle, thus far, is the miniaturization of such robotic devices to make them fit into the brain's blood vessels, which are considerably smaller and more tortuous than those in other body parts. For example, existing continuum robots are limited to relatively large scale (>3 mm in diameter) due to miniaturization challenges inherent in their conventional actuation mechanisms. Tendon-driven continuum robots with antagonistic pairs of wires are generally difficult to scale down to submillimeter size in diameter due to the increasing complexities in the fabrication process as the components become smaller. Magnetically steerable continuum robots have also remained at large scales due to the finite size of the embedded magnets required to generate adequate deflection under applied magnetic fields. Additional limitations associated with the use of such rigid magnets, particularly at submillimeter scale, are epitomized by the fact that several products of magnet-tipped microguidewires seeking FDA premarket approval were later recalled because of the concern that the tiny magnets at the tip could break off, which may lead to undesired clinical problems. The miniaturization challenges have rendered even the most advanced form of commercialized continuum robots, mostly used for cardiac and peripheral interventions, substantially unsuited for neurosurgical applications due to the considerably smaller and more tortuous vascular structures involved (FIGS. 2 C-D). Internal carotid arteries are already smaller than 5 mm in diameter, while cerebral arteries are typically smaller than 2.5 mm in diameter (FIG. 2D), which makes it almost impossible to use bulky robotic catheters.

Another challenge with current devices is posed by the use of X-ray for fluoroscopic imaging, which visualizes the state of the guidewire in real time during the operation (FIG. 1D). Being exposed to continuous X-ray for a short period of time is generally considered innocuous for patients. However, for neuroradiological interventionalists, cumulative radiation exposure can pose a potential health threat, because the protective gears cannot perfectly block the radiation.

Thus, further improvements in both devices and methods of use are greatly needed.

SUMMARY OF THE INVENTION

The present invention provides a device for use in navigating through highly constrained environments, such as narrow and tortuous vasculature, based on active omnidirectional steering upon magnetic actuation. In particular, the present invention provides a submillimeter-scale ferromagnetic soft continuum robotic device having an elongate body (generally in the form of a guidewire) composed of soft polymer matrices with dispersed hard-magnetic microparticles. An inner core is concentrically disposed within the soft polymer material along at least a portion of the elongate body to provide further support and pushability of the device when navigating a desired pathway. This inner core can be in the form of a wire, which primarily provides support to the soft polymer matrix material, or it can be configured to provide the soft continuum robotic device with additional functionalities, e.g. by incorporating an optical fiber core for laser delivery.

According to one aspect, the present invention provides a continuum robotic device for use in minimally invasive procedures comprising: an elongate body having a proximal end, a distal end, an inner core and an outer shell; the outer shell fabricated of an elastomeric material; a plurality of ferromagnetic particles dispersed within the outer shell; the elongate body having an initial shape. According to this aspect, the elongate body has an outer diameter of no greater than about 1000 μm, and exposure of the device to an external magnetic field magnetically activates the plurality of ferromagnetic particles to provide the elongate body in an activated shape different than the initial shape.

According to another aspect, the present invention provides a method of performing a minimally invasive procedures on the microvascular system comprising: providing a continuum robotic device comprising an elongate body having a proximal end and a distal end, the elongate body including an inner core and an outer shell; the outer shell fabricated of an elastomeric material; a plurality of ferromagnetic particles dispersed within the outer shell; and the elongate body having an initial shape; inserting the distal end into a blood vessel connected to one or more target sites of the microvascular system; and actively guiding the distal end and advancing the elongate body through the microvascular system, including nonlinear branches of the microvascular system, to the one or more target sites using an external magnetic field to activate the plurality of ferromagnetic particles, wherein the external magnetic field is selectively applied to the elongate body. According to this embodiment, selectively exposing the elongate body to one or more external magnetic fields is carried out so as to provide the elongate body in a variety of activated shapes configured to guide the distal end and advance the elongate body through microvascular system to the one or more target sites.

Embodiments according to these aspects may include one or more of the following features. Exposure of the device to an external magnetic field magnetically activates the plurality of ferromagnetic particles to provide omnidirectional steering of the device. The plurality of ferromagnetic particles are uniformly magnetized along an axial direction of the elongate body. The plurality of ferromagnetic particles are magnetized in nonuniform patterns of magnetic polarity along an axial direction of the elongate body. The plurality of ferromagnetic particles are magnetized in patterns of magnetic polarity comprising alternating patterns of different magnetic polarities. Alternating patterns of different magnetic polarities are disposed such that exposure of the device to an external magnetic field magnetically activates the plurality of ferromagnetic particles to provide the elongate body in a wavy shape. The inner core and outer shell and fabricated, and the plurality of ferromagnetic particles are dispersed, such that exposure of the device to various direction and magnitudes of external magnetic fields provides the body in a variety of activated shapes different than the initial shape. The elongate body has an outer diameter no greater than about 900 μm, more preferably no greater than about 850 μm, more preferably no greater than about 800 μm, more preferably no greater than about 750 μm, more preferably no greater than about 700 μm, more preferably no greater than about 650 μm, and more preferably no greater than about 600 μm. The device further comprises a hydrogel skin disposed on the outer shell. The hydrogel skin has a thickness of about 10 μm to about 25 μm. The ferromagnetic particles have an average particle size of about 2 μm to about 10 μm. The inner core is a metallic wire. The metallic wire is fabricated of superelastic nickel-titanium, stainless steel, platinum, a platinum-tungsten alloy, a cobalt-chromium-molybdenum alloy, or combinations thereof. The inner core comprises one or more optical fibers. The elongate body further includes one or more imaging, illumination, laser delivery, or sensing elements at or near the distal end. The inner core is a fiber optic shape sensor. The inner fore is a fiber optic shape sensor comprising one or more Bragg grating. The outer shell is fabricated of one or more polymer materials having a Young's modulus below 20 MPa. The outer shell is fabricated of an elastomer. The outer shell is fabricated of one or more materials selected from natural rubbers, synthetic rubbers, and thermoplastic elastomers. The outer shell is fabricated of one or more materials selected from silicone rubber, polyacrylate rubber, thermoplastic polyurethane, and styrene-ethylene-butylene-styrene (SEBS). The plurality of ferromagnetic particles are selected from neodymium iron boron (NdFeB), samarium cobalt (SmCo), aluminum-nickel-cobalt (AlNiCo), copper-nickel-iron (CuNiFe), barium-iron oxide (BaFeO), platinum-cobalt alloys, and combinations thereof. The ferromagnetic particles have programmed magnetic polarities that enable magnetic actuation upon exposure to an external magnetic field. The plurality of ferromagnetic particles are coated with a non-corrosive layer. The non-corrosive layer is fabricated of one or more materials selected from silica, Parylene C, gold, and epoxies. The inner core extends through a portion of the elongate body that is less than an entire length of the elongate body. A portion of the elongate body at the distal end does not include the inner core. The inner core tapers in diameter towards the distal end of the elongate body. The elongate body comprises one or more magnetically active portions comprising one or more outer shell portions containing a plurality of ferromagnetic particles dispersed therein, and one or more inactive portions comprising one or more one or more outer shell portions not containing a plurality of ferromagnetic particles dispersed therein. A distal end portion of the elongate body comprises a distal magnetically active portion, and an adjacent portion of the elongate body proximal the distal magnetically active portion comprises a magnetically inactive portion. Selectively exposing the elongate body to one or more external magnetic fields creates multiple controllable modes and degrees of bending of the elongate body depending on a direction and strength of the external magnetic field. A user performs the method remotely by viewing the device within the microvascular system using real time imaging, and applying the one or more external magnetic fields using a robotic manipulation platform. The minimally invasive procedure is a cerebrovascular or endovascular procedures. The one or more target sites are selected from one or more aneurysms, embolisms, lesions, or arteries. The device inner core comprises one or more optical fiber, and the device further includes a laser delivery element at the distal end, and the method further comprises guiding and advancing the distal end to one or more target sites selected from vascular occlusions, atherosclerosis, aneurysms, embolisms, and lesions, and treating the one or more target sites with the laser. The device inner core comprises one or more optical fiber, and the device further includes one or more imaging, sensing, and/or illumination elements, and the method further comprises providing imaging, sensing, and/or illumination while guiding the distal end and advancing the elongate body through the microvascular system to the one or more target sites. The device inner core comprises one or more fiber optic shape sensors, and the method further comprises using the one or more fiber optic shape sensors to provide a user with real-time feedback of a 3D shape of the elongate body. The one or more fiber optic shape sensors comprise one or more Bragg grating, and the method further comprises exposing the one or more Bragg grating to strain or temperature to shift a wavelength of the Bragg grating, and determining a direction and magnitude of the shift.

According to another aspect, the present invention provides a system for performing a minimally invasive procedures on the microvascular system comprising a continuum robotic device for use in minimally invasive procedures comprising: an elongate body having a proximal end, a distal end, an inner core and an outer shell; the outer shell fabricated of an elastomeric material; a plurality of ferromagnetic particles dispersed within the outer shell; the elongate body having an initial shape; wherein the elongate body has an outer diameter of less than about 1000 μm; and a control mechanism comprising a single permanent magnet held and manipulated by a multi-degree of freedom (DOF) robotic arm, wherein exposure of the continuum robotic device to an external magnetic field from the control mechanism magnetically activates the plurality of ferromagnetic particles to provide the elongate body in an activated shape different than the initial shape.

Other systems, methods and features of the present invention will be or become apparent to one having ordinary skill in the art upon examining the following drawings and detailed description. It is intended that all such additional systems, methods, and features be included in this description, be within the scope of the present invention and protected by the accompanying claims.

BRIEF DESCRIPTION OF THE DRAWINGS

The accompanying drawings are included to provide a further understanding of the invention, and are incorporated in and constitute a part of this specification. The components in the drawings are not necessarily to scale, emphasis instead being placed upon clearly illustrating the principles of the present invention. The drawings illustrate embodiments of the invention and, together with the description, serve to explain the principals of the invention.

FIG. 3C illustrates navigation in the cerebrovasculature with a device according to an embodiment of the present invention based on magnetically controlled active steering to enable access to difficult-to-reach environments such as cerebral aneurysms, and FIG. 3D illustrates laser atherectomy using an embodiment of the present invention which incorporates a laser delivery into the core to remove mechanical clots (thrombus) or plaque that cause obstructive vascular diseases.

FIGS. 6A-C schematically illustrate a soft continuum robotic device having an incorporated optical fiber as a functional core according to an embodiment of the present invention together with an experimental demonstration of the steerable laser delivery capability, with FIG. 6B illustrating the experimental setup for demonstrating steerable laser delivery, and FIG. 6C illustrating close views of the laser-emitting tip which accurately points the small targets (2-mm dots) with the laser beam in a prescribed order based on omnidirectional magnetic steering.

FIGS. 9A-B illustrate an experimental demonstration of a soft continuum robotic device according to an embodiment of the present invention as it navigates through a nonlinear path formed by a series of loosely spaced rings using active steering based on magnetic actuation.

FIG. 12A shows a soft continuum robotic device emitting a laser beam at different target sites in a carotid artery phantom based on magnetic steering, and FIG. 12B shows navigation downstream through the carotid artery after turning off the laser.

FIG. 13B graphically illustrating the storage modulus plotted against the applied shear stress for permanently magnetized composite inks with 10 vol % (bottom curve), 20 vol % (middle curve), and 30 vol % (top curve) of NdFeB dispersed in uncured PDMS resin, where the crossover point at which the storage modulus becomes smaller than the loss modulus defines the shear yield stress beyond which the magnetized composite paste can flow. The identified shear yield stresses for 20 vol % and 30 vol % inks are 165 kPa and 1640 kPa, respectively. The shear yield stress for 10 vol % ink is smaller than the lower bound of the applied shear stress, and hence the data shows that the ink is already fluidized due to the applied shear stress, and FIG. 13C graphically illustrating apparent viscosity plotted against the applied shear rate for 10 vol % (bottom curve), 20 vol % (middle curve), and 30 vol % (top curve) inks. The data reveals shear-thinning behavior of the thixotropic paste of magnetized ferromagnetic composite ink, and FIGS. 13D-E illustrate the presence of shear yield stresses in 20 vol % magnetized inks helps prevent their phase separation due to gravitational sedimentation of the dispersed particles over time where the vial on the left contains nonmagnetized, freely flowing composite ink, the middle vial contains already magnetized composite ink, and the right vial contains nonmagnetized ink first loaded and then magnetized.

FIG. 14B shows a micro-computed tomography image of solidified ferromagnetic composite based on PDMS and silica-coated NdFeB particles showing uniformly dispersed particles with no obvious gradient due to sedimentation, FIG. 14C shows a scanning electron microscope image of silica-coated NdFeB particles indicating the size of a single particle, FIG. 14D shows a transmission electron microscope image of a silica coated NdFeB particle, from which the thickness of the silica layer is identified to be 10 nm, FIG. 14E shows Fourier transform infrared spectroscopy of silica-coated NdFeB particles clearly indicating the presence of Si—O—Si bonds, FIG. 14F shows the results of leaching test of both uncoated and coated NdFeB particles in 0.2 mM HCl solution (pH 3.7) for 3 days, where no visible change was observed in the silica-coated particles owing to the presence of the protective silica layer, whereas the uncoated particles were highly oxidized, turning the color of the solution yellow.

FIG. 15B shows an uncoated specimen without hydrogel skin, where the dashed line indicates the boundary of the cross-section of the uncoated specimen, FIG. 15C shows top views of the coated specimen with hydrogel skin, FIG. 15D shows the same top view of an uncoated specimen, where the fluorescing specks visible in the uncoated sample are due to residual fluorescein adsorbed onto the surface, FIG. 15E shows a schematic of testing setup for measuring friction coefficients using a rheometer, FIG. 15F shows a schematic of testing setup for measuring force required to pull a cylindrical specimen (diameter of 8 mm) at a constant speed under applied normal force by the pair of grips, FIG. 15G shows a semi-log plot of the pulling force measured over time during the pullout test performed at 200 mm/min for both coated and uncoated specimens under two different normal force conditions (2 N and 5 N), FIG. 15H shows friction coefficients measured from both coated and uncoated samples under different shear rates and FIG. 15I under normal pressure, FIG. 15J showing friction coefficients measured from prolonged shearing of both coated and uncoated samples up to 60 min at shear rate of $0.5\ s^{-1}$ under normal pressure of 6 kPa. The error bars in FIGS. 15H-J indicate the standard deviations of the mean values obtained from 5 different measurements.

FIG. 17A shows a set of rings loosely placed at different locations (in mm) with different heights (in mm) and tilt angles, through which the devices navigate selectively based on the demonstrated active steering capabilities, and FIG. 17B shows set of rings more tightly placed to form a tortuous path.

FIGS. 18A-B show a magnetic actuation and steering mechanism based on a cylindrical permanent magnet, where FIG. 18A shows a schematic of a cylindrical magnet of radius R and height H and the magnetic field around the magnet, and FIG. 18B schematically depicts a basic principle for magnetic actuation and steering of the present invention ferromagnetic soft continuum robotic devices employed in the experimental demonstrations herein, where the central axis of the magnet is aligned along the desired direction to induce the bending actuation on the device's magnetically responsive tip along the desired direction. The degree of bending, which is determined by the applied field strength, is controlled by adjusting the distance between the magnet and the robot.

FIG. 20A is a detailed view and relevant dimensions of the vascular structure of the phantom model around a particular cerebrovascular anatomy (the circle of Willis), as well as the surrounding arteries with multiple aneurysms. The path that is navigated, from the carotid artery to the right middle cerebral artery, is indicated with dashed lines, FIG. 20B illustrates the vascular anatomy and dimensions of the real-sized phantom model (top view), and FIG. 20C illustrates the vascular structure and dimensions of the phantom model (side view) around the path.

DETAILED DESCRIPTION

Figure 1A:
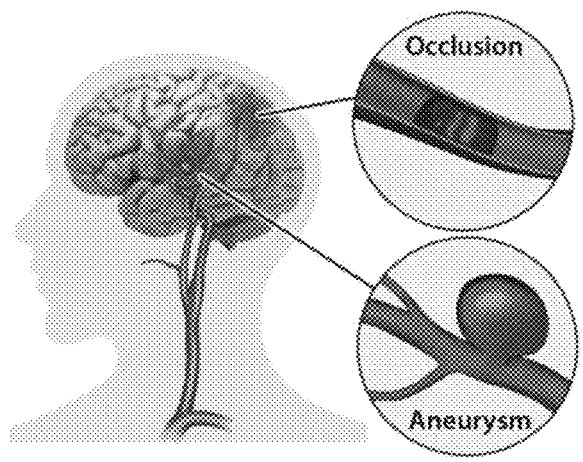
FIGS. 1A-D schematically illustrate the challenges in current cerebrovascular and endovascular neurosurgery, with FIG. 1A illustrating pathologic conditions in cerebrovascular arteries that can lead to either ischemic (occlusion by a mechanical clot) or hemorrhagic (bleeding due to aneurysm rupture) stroke, FIG. 1B illustrating manually controlled, passive guidewires used for providing minimally invasive access to targeted lesions, FIG. 1C depicting two different types of manual guidewires with a pre-bent tip (left) and re-shapeable tip (right) for twisting-based, passive steering for navigating the narrow and highly nonlinear vascular structures, and FIG. 1D illustrating C-arm fluoroscopy required for real-time imaging in endovascular neurosurgery based on continuous X-ray, to which the surgeons are repeatedly exposed during their careers.
Figure 1B:
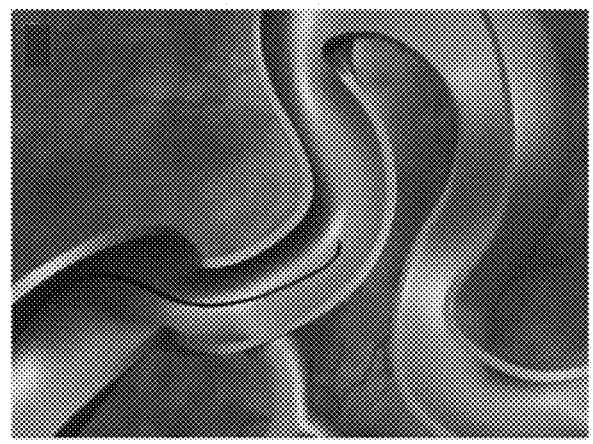
Figure 1C:
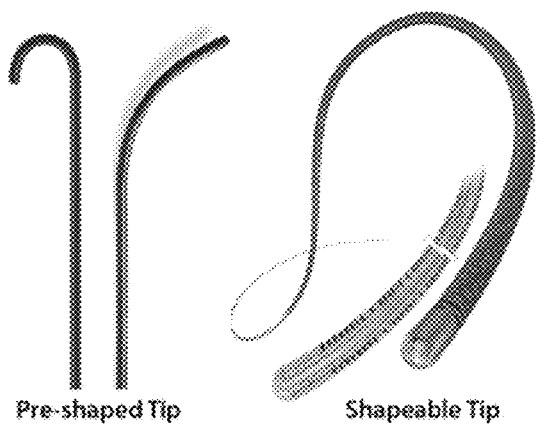
Figure 1D:
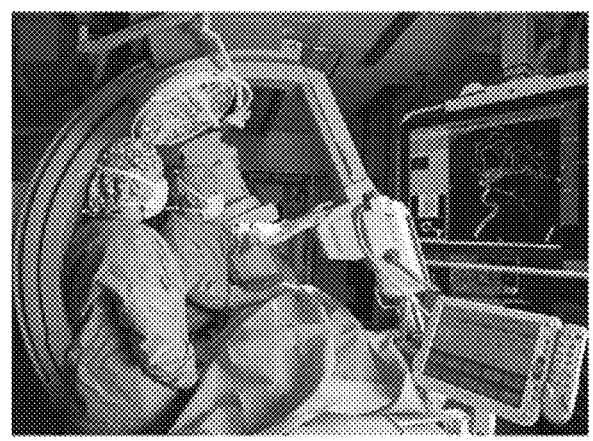

The present invention generally provides a device and method for use in minimally invasive procedures, particularly procedures on the vascular system including cerebrovascular and endovascular neurosurgical procedures. More particularly, the present invention provides a submillimeter-scale soft continuum robotic device adapted for navigating the complex vascular system, including the microvascular system. The device is provided with omnidirectional steering and navigating capabilities based on magnetic actuation, which are enabled by programmed magnetic polarities in the soft body of the device. An outer surface of the device may be provided with a material, such as a hydrogel skin, to minimize friction as the device navigates through complex and constrained environments, such as a tortuous cerebrovascular system with multiple aneurysms.

The present invention small-scale soft continuum robotic device, which is provided with self-contained actuation and intuitive manipulation, enables access to hard-to-reach areas and, thus, provides numerous benefits in diverse areas, particularly in medical applications such as minimally invasive surgery.

Reference will now be made in detail to embodiments of the present invention, examples of which are illustrated in the accompanying drawings. Wherever possible, the same reference numbers are used in the drawings and the description to refer to the same or like parts.

According to an embodiment of the present invention, a soft continuum robotic device 1 is generally provided with an elongate body 2 in the general form of a guidewire. The elongate body 2 includes a core-shell type structure in which an inner core 3 is disposed within and surrounded by an outer shell 4. Dispersed within the outer shell 4 are ferromagnetic particles 6 as distributed actuation sources to enable navigation and control of the soft continuum robotic device 1 through the application of an external magnetic field.

Because the present invention is directed towards and used in minimally invasive procedures (e.g., targeting lesions in intracranial arteries), particularly wherein microvascular structures must be navigated, the elongate body 2 is suitably provided with a diameter that is suitably sized to navigate the small and non-linear pathways, and is fabricated of materials that provide the required bendability and manipulation of the elongate body 2 along its length. As such, according to preferred embodiments of the invention, the elongate body 2 has an overall diameter no greater than about 2500 µm, more preferably no greater than about 2000 µm, more preferably no greater than about 1500 µm, more preferably no greater than about 1000 µm, more preferably no greater than about 950 µm, more preferably no greater than about 900 µm, more preferably no greater than about 850 µm, 800 µm, more preferably no greater than about 750 µm, more preferably no greater than about 700 µm, more preferably no greater than about 650 µm, and more preferably no greater than about 600 µm. According to an exemplary embodiment, the overall diameter of the elongate body 2 ranges from about 250-1000 µm, and in some embodiments, from about 250-600 µm. Due to the core-shell structure of the guidewire, the overall diameter is at least as large as the internal core 3 required to provide adequate structure to the elongate body 2, plus the outer shell 4 layer which accommodates the ferromagnetic particles 6. Typically, internal cores of guidewires range in diameter from about 80-400 µm. In embodiments where typical internal guidewire core sizes are used for the inner core 3, the outer shell 4 will generally make up the remainder of the total overall diameter. As noted, in some embodiments a hydrogel skin is provided on the outermost surface of the elongate body 2. Such hydrogel skin layers are generally thin (e.g. 10-25 µm) layers. As such, in certain embodiments, where the above-noted ranges for the overall diameter and inner core 3 apply, the outer shell 4 plus the hydrogel skin will generally make up the remainder of the total overall diameter.

As illustrated, the inner core 3 is disposed within and is entirely surrounded by the outer shell 4 (e.g. see FIGS. 3A-B, 6A, 7B). The inner core 3 is equipped with additional mechanical support and/or functionalities, to provide a functional core structure. For example, in order to provide mechanical support and pushability required for navigating the elongate body 2 through complex and narrow pathways, the inner core 3 is generally in the form of a wire. According to various embodiments, the inner core 3 is in the form of a thin metallic wire. On preferred example of a suitable thin metallic wire is a superelastic nickel-titanium (nitinol) wire, or other metallic alloys. However, the inner core 3 may be suitably be fabricated of any other materials conventionally used in forming the wire portions of conventional guidewires, including but not limited to stainless steel, platinum, platinum-tungsten alloy, cobalt-chromium-molybdenum alloy, Scitanium®, MP35N® alloys, etc.

If it is desired to provide further functionalities to the soft continuum robotic device 1, a variety of functional inner cores 3 may be incorporated within the outer shell 4. For example, the inner core 3 may be formed of one or a bundle of optical fibers 5 to enable additional functions such as imaging, illumination, or laser delivery (e.g., see FIGS. 3B, 6A). As such, the present invention soft continuum robotic device 1 will be capable of delivering a laser beam through the embedded optical fiber along its elongate body 2 (FIGS. 3B, 6A). It is noted that since the transmission of light through the incorporated optical fibers 5 is not affected by the externally applied magnetic fields for actuation, the soft continuum robotic device 1 can still be magnetically actuated and steered to enable the navigational tasks. Potential applications of such multifunctional soft continuum robots include laser-assisted treatment of vascular occlusion (blockage due to a thrombus) or atherosclerosis (narrowing due to plaque buildup), so-called laser atherectomy (e.g., FIG. 3D). The ability to keep the laser-emitting tip of the soft continuum robotic device 1 in position based on magnetic steering will minimize unwanted motion or displacement of the tip from the desired location during the laser ablation, thereby improving the accuracy and the safety of such procedures.

Based on the omnidirectional steering capability, a soft continuum robotic device 1 equipped with an optical fiber inner core 3 was used to demonstrate magnetically steerable laser delivery (see FIGS. 6A-C). As depicted, the soft continuum robotic device 1 was manipulated using magnetic actuation so as to accurately point the laser beam at the small targets in a desired order.

According to some embodiments, an optical fiber inner core 3 is provided in the form of a fiber optic shape sensor configured to facilitate monitoring and tracking the shape of the elongate body 2. The present invention inner core 3 in the form of a fiber optic shape sensor can be structured and configured in accordance with any conventional fiber optic shape sensors. Incorporating this shape-sensing capability into the present invention soft continuum robotic device 1 can provide a user with an improved ability to more accurately navigate and control the device using an external magnetic field. In particular, providing the inner core 3 in the form of a fiber optic shape sensor enables real-time feedback of the 3D shape of the elongate body 2 for better tracking, steering, and navigational purposes.

According to an exemplary embodiment, the fiber optic shape sensor is in the form of a Fiber Bragg Grating (FBG) array, which is generally a microstructure that is patterned in the core of a fiber optic. Any number of FBG's may be patterned along the length of a fiber optic, with each FBG providing an invisible reflector disposed inside the core of the optical fiber with specific working wavelength. FBG arrays are known in the art and, thus, the present invention fiber optic shape sensor may be in accordance with any of these known FBG array structures and configurations. Upon exposure of the FBG array to strain or temperature, the Bragg wavelength of the FBG shifts (either increases or decreases), where the direction and magnitude are determined by the change in the applied strain or temperature.

The shape-sensing capability provided by the present invention will, thus, enable (1) using a full 3D roadmap (instead of the current 2D roadmaps) in various procedures (including endovascular and endoscopic procedures) while minimizing radiation exposure due to the reduced use of fluoroscopy based on continuous X-ray and (2) more precise and accurate control of continuum robotic devices as a consequence of the ability to implement feedback control, which is enabled by the state-awareness through the embedded shape sensors.

In addition to laser delivery functionalities, the inner core 3 can be suitably designed to provide a number of other applications. For instance, when equipped with a miniature CMOS sensor, while having multiple functional cores for both illumination and imaging, the soft continuum robotic device 1 may further enable submillimeter-scale endoscopic procedures such as angioscopy to better diagnose pathologic conditions such as embolism or aneurysms in the affected sites of intracranial arteries. Such sites are far less accessible due to the considerably small and tortuous vascular structures.

As set out, the elongate body 2 of the soft continuum robotic device 1 includes an outer shell 4. Generally, the outer shell material 4 can be selected from any materials that provide the necessary maneuverability and flexibility to the elongate body 2 so that the elongate body can navigate narrow and complex vascular pathways discussed herein. According to embodiments of the present invention, the outer shell 4 is fabricated of one or more soft polymer matrix materials. In principle, any elastomer (soft polymers with low Young's modulus; e.g. below 20 MPa) could suitably be used, and is limited only by the upper stiffness value at which adequate bending and manipulation of the elongate body 2 would not be possible upon magnetic actuation. For example, some suitable materials for use as the outer shell 4 material include, but are not limited to, natural/synthetic rubbers (e.g. silicone rubber, polyacrylate rubber, etc., which would be crosslinked (vulcanized)) and thermoplastic elastomers (thermoplastic polyurethane, styrene-ethylene-butylene-styrene (SEBS), etc., which are melt-processible and do not require crosslinking). According to some embodiments, the outer shell 4 could be formed using commercial guidewire fabrication methods, e.g., by using a typical jacketing process based on extruding polymer melts (e.g. TPU) around a core wire (inner core 3). Because the soft continuum robotic device 1 is used by inserting the elongate body 2 within the vasculature of a patient, the all materials used in forming the soft continuum robotic device 1, and especially the outer shell 4 are biocompatible.

Figure 3A:
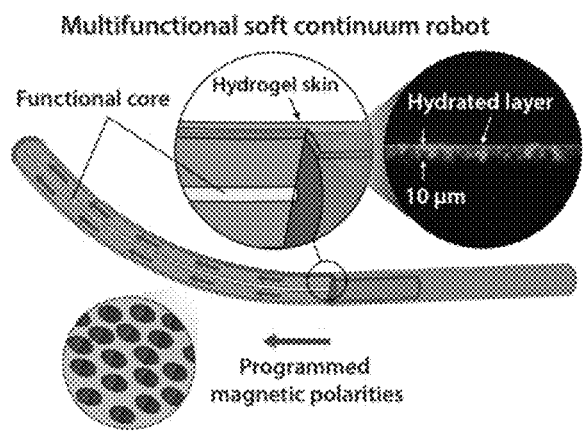
FIGS. 3A-D schematically illustrate multifunctional soft continuum robotic devices for use in cerebrovascular and endovascular procedures, with FIG. 3A illustrating the incorporation of a concentric functional core and a hydrogel skin coating on the outer surface of the core to provide a self-lubricating layer to reduce the friction while navigating through complex and constrained environments according to an embodiment of the present invention, FIG. 3B illustrating the incorporation of a functional core in the form of an optical fiber to provide magnetically steerable laser delivery or imaging for minimally invasive medical applications according to an embodiment of the present invention.
Figure 3B:
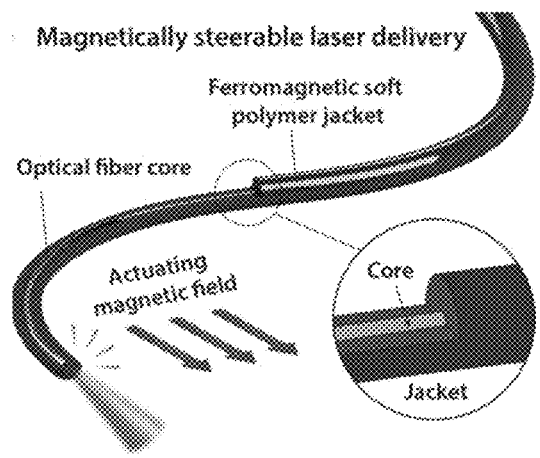
Figure 3C:
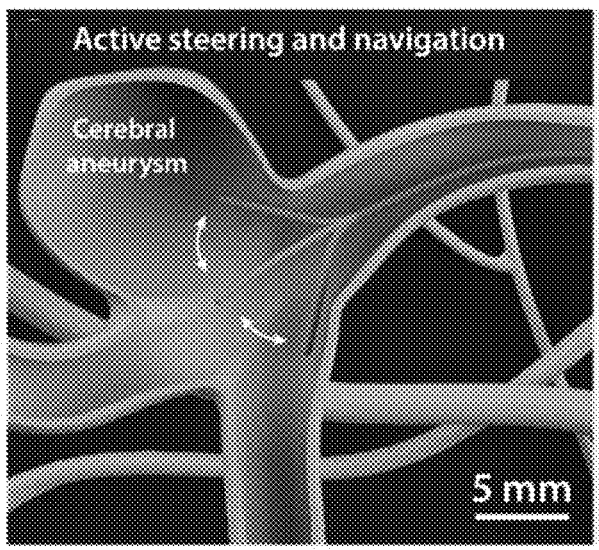
Figure 3D:
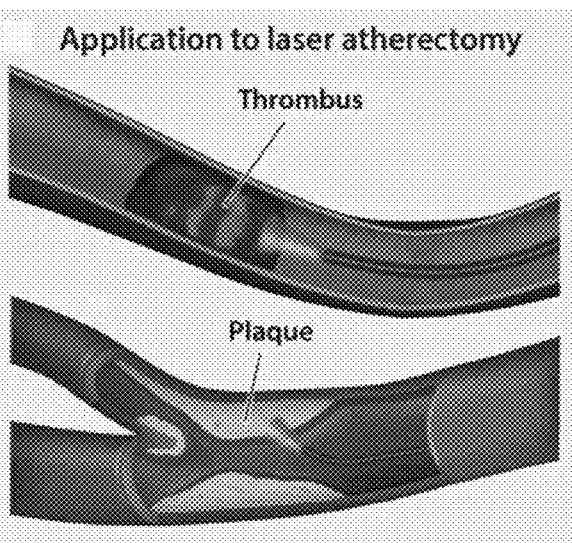
Figure 5A:
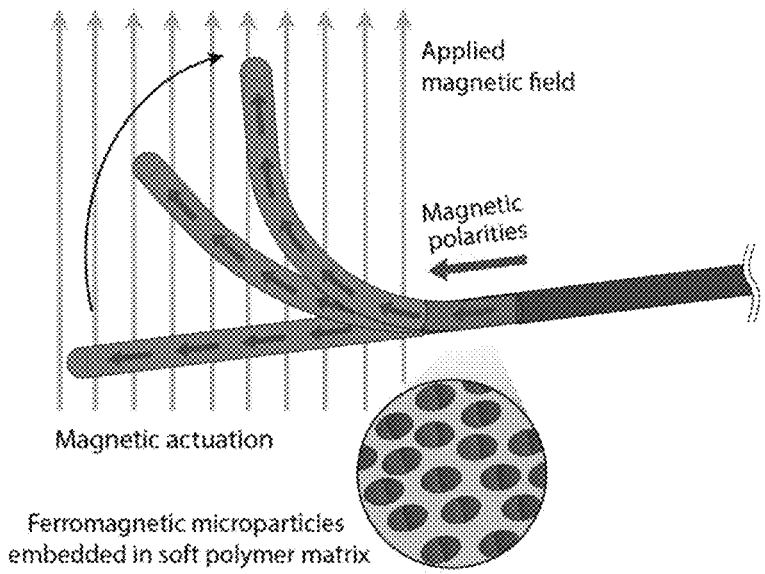
FIGS. 5A-B schematically illustrate a magnetically steerable soft continuum robotic device according to embodiments of the present invention, with FIG. 5A showing a magnetically responsive elongate body which deflects along an externally applied magnetic field due to the incorporation of ferromagnetic microparticles with programmed magnetic polarities along the axial direction, and FIG. 5B illustrating a ferromagnetic soft continuum robotic device according to an embodiment of the present invention with programmed magnetic polarities resulting from the hard-magnetic particles embedded in the elongate soft polymer matrix body, where a hydrogel skin provides a hydrated, self-lubricating layer on the device's surface, and where a silica shell coated around the embedded magnetic particles prevents their corrosion at the hydrated interface.
Figure 5B:
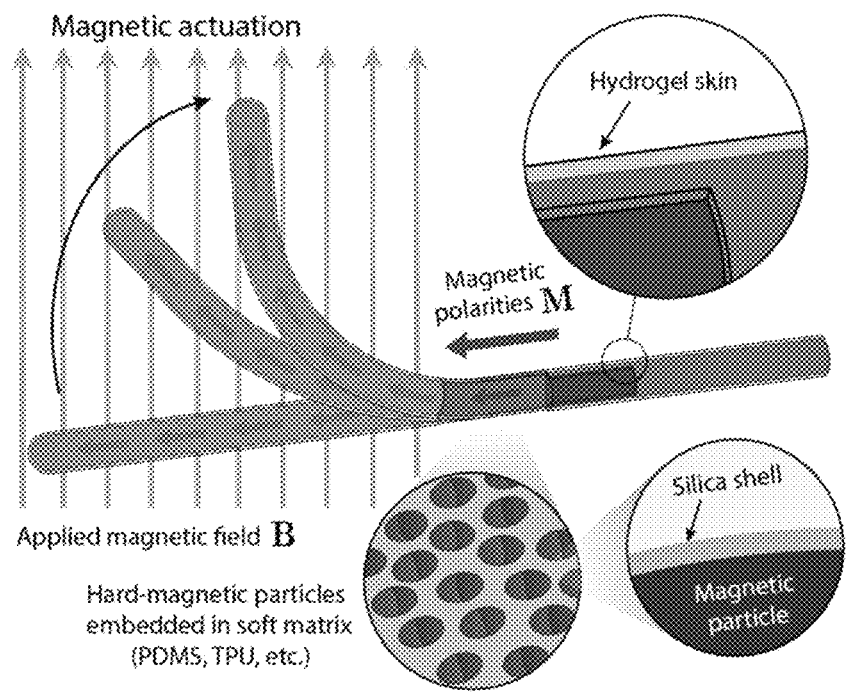

In order to provide the soft continuum robotic device 1 with remote control capabilities via magnetic fields, a plurality of magnetizable ferromagnetic particles 6 (preferably microparticles) are dispersed within the outer shell 4 material (e.g., see FIGS. 3A, 5A-B). Some examples of suitable magnetizable ferromagnetic particles 6 include, but are not limited to, neodymium iron boron (NdFeB), samarium cobalt (SmCo), aluminum-nickel-cobalt (AlNiCo), copper-nickel-iron (CuNiFe), barium-iron oxide (BaFeO), platinum-cobalt alloys, and combinations thereof. The magnetizable ferromagnetic particles 6 are provided with magnetic polarities that enable magnetic actuation when external fields are applied (e.g., see FIGS. 5A-B)

Figure 14A:
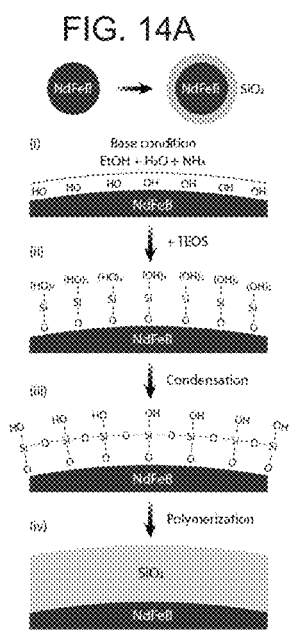
FIGS. 14A-F illustrate the characterizations of silica-coated magnetic particles, with FIG. 14A showing a schematic of the polycondensation reaction of TEOS in the presence of catalysts in basic conditions, where the nucleation and polymerization of TEOS lead to crosslinked layer of silica around the NdFeB particles.
Figure 14B:
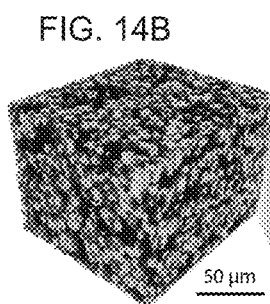
Figure 14C:
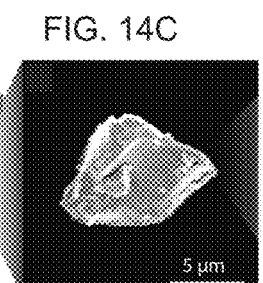
Figure 14D:
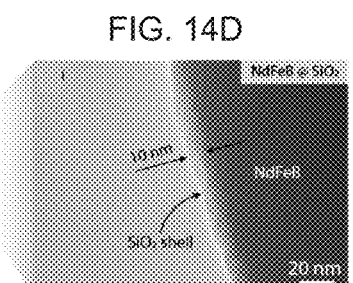
Figure 14E:
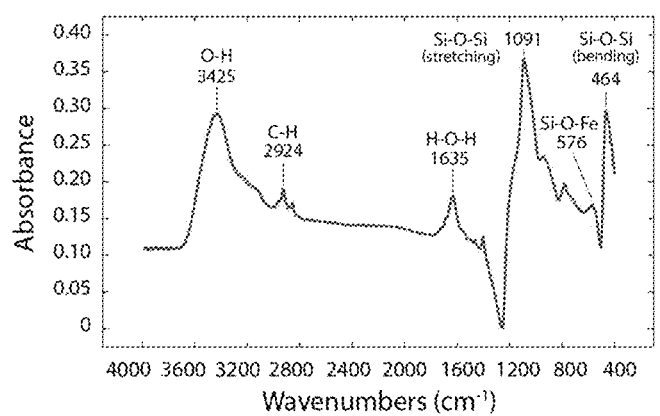
Figure 14F:
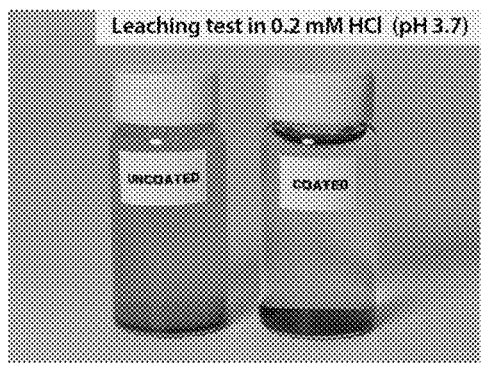

Ferromagnetic alloys, in general, have highly corrosive nature due to the high content of iron. In embodiments which include a hydrogel skin on an outer surface of the elongate body 2, in order to prevent corrosion of the embedded ferromagnetic particles (e.g., NdFeB) at the hydrated interface with the water-containing hydrogel skin, the ferromagnetic particles are coated with a thin shell of non-corrosive material. Any conventional non-corrosive material may be suitably be used and may include, for example, silica (glass). Parylene C, as well as a variety of non-corrosive and non-magnetic metals (e.g., gold etc), as well as epoxies. One example of a non-corrosive material is silica (FIG. 5C) based on the condensation reaction of tetraethylorthosilicate (TEOS), which nucleates around the particles to form a crosslinked silica layer (FIG. 14A). The resulting silica shell was identified to be about 10-nm thick from transmission electron microscope (TEM) imaging (FIG. 14D) and as further verified by Fourier transform infrared spectroscopy, which clearly indicates the presence of Si—O—Si bonds (FIG. 14E). The effectiveness of the silica shell in preventing the corrosion of NdFeB particles was verified by performing a leaching test for both coated and uncoated particles with a weak acidic solution (0.2 mM HCl; pH 3). The results showed highly oxidized uncoated particles but no visible change in silica-coated particles, which illustrated the anti-corrosion effect of the silica shell formed around the NdFeB particles (FIG. 14F). Due to the marginal thickness of the silica shell that was formed as compared to the size of microparticles, the silica coating resulted in a slight increase in volume, which was roughly estimated to be around 1% when assuming a uniform silica layer around a spherical ferromagnetic particle.

By incorporating the ferromagnetic particles 6 into the outer shell 4, the present invention soft continuum robotic device 1 is provided with active, omnidirectional steering upon magnetic actuation, which is based on the deformation of the magnetically active elongate body 2 in response to the externally applied magnetic field. Using this magnetic steerability, the soft continuum robotic device 1 can be selectively navigated through desired paths.

According to various embodiments, in order to further reduce friction generated when the soft continuum robotic device 1 navigates through complex and constrained environments, the surface of the elongate body 2 can be coated with a thin, lubricious layer of hydrophilic polymers (e.g., see FIGS. 3A, 5B). Such hydrophilic coatings may be in accordance with conventional hydrophilic coatings provided on medical devices, and could further be applied using any convention hydrophilic coating technique. For example, according to an exemplary embodiment, a hydrogel skin may be grown to provide a thin (e.g. 10-25 µm) layer of hydrated crosslinked polymers onto the surface of the elongate body 2. This hydrogel skin substantially decreases the surface friction (e.g., by more than 10 times) due to its high water content.

According to an exemplary embodiment, the hydrogel skin is formed of a crosslinked network of hydrophilic polymers (polydimethylacrylamide; PDMAA) that are grafted onto the elastomer chains on the elongate body 2 surface. For the hydrogel coating procedure, the following protocol may be followed: First, the solidified elongate body 2 is treated with an organic solution based on ethyl alcohol that contains hydrophobic photoinitiators (benzophenone). Exposure to this organic solution induces swelling-driven absorption of the photoinitiators into the elongate body 2 surface. The treated elongate body 2 is then immersed into a hydrogel monomer (DMAA) solution (FIG. 7D) containing hydrophilic photoinitiators (Irgacure-2959). Upon exposure to ultraviolet (UV) radiation (FIG. 7D), the hydrogel monomers are polymerized by the hydrophilic initiators while at the same time covalently grafted onto the surface-bound elastomers by the activated benzophenone, leaving a thin hydrogel-polymer interpenetrated layer on the surface. The thickness of the hydrogel skin is measured to be 10-25 µm from fluorescence microscope images taken from coated and uncoated samples with planar geometry (1-mm-thick sheet) (FIG. 15A-D). The microscopic images clearly identify the presence of the hydrogel skin on the coated samples.

Figure 15A:
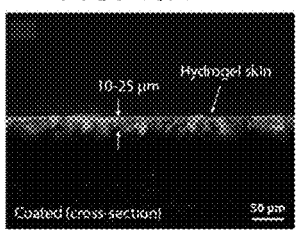
FIGS. 15A-J illustrate a hydrogel skin as a lubricating layer, with FIG. 15A showing cross-sectional views of the coated specimen of PDFM+NdFeB (20 vol %) with hydrogel skin visualized by absorbed fluorescein.
Figure 15B:
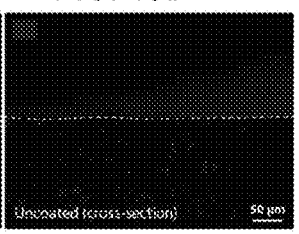
Figure 15C:
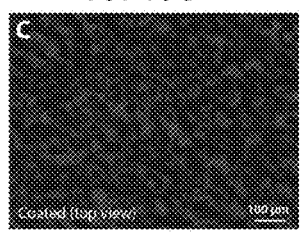
Figure 15D:
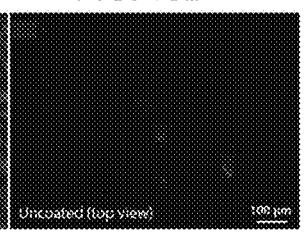
Figure 15E:
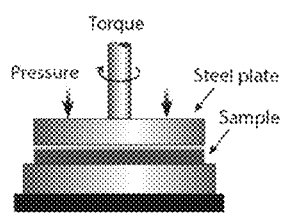
Figure 15F:
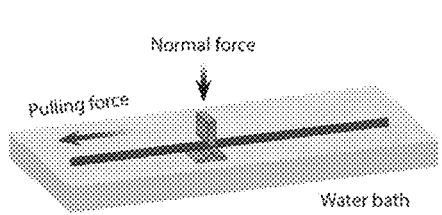
Figure 15G:
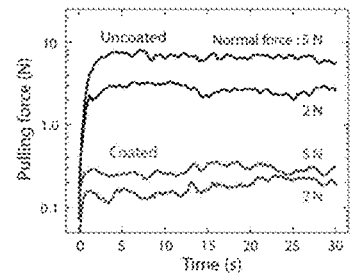
Figure 15H:
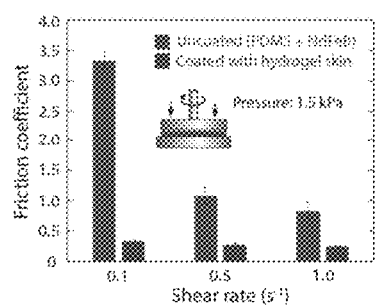
Figure 15I:
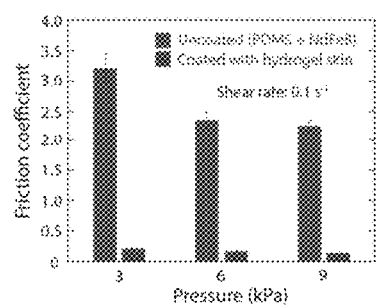
Figure 15J:
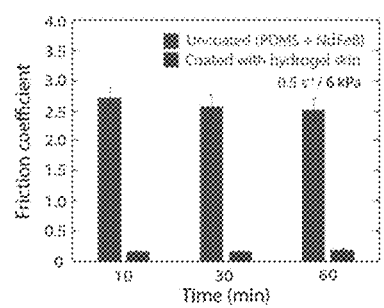

The resulting hydrogel skin was shown to dramatically reduce the surface friction, which is characterized by the friction coefficients measured from a rheometer testing while applying different levels of shear rates and normal pressure (FIG. 15E). The measurements show a tenfold decrease in the friction coefficient (FIGS. 15H-I) as a result of the lubricious hydrogel skin in all given conditions. Furthermore, the coated hydrogel skin was demonstrated to remain stable and undamaged even after prolonged shearing over an hour, exhibiting sufficient mechanical robustness (FIG. 15J). Forces required to pull cylindrical specimens with and without hydrogel skins were also experimentally measured at a constant speed (200 mm/min) under different normal forces (2 N and 5 N) applied by a pair of grips (FIG. 15F). The results show substantial decrease in the pulling force as a consequence of the self-lubricating hydrogel skin (FIG. 15G). When the applied normal force was 2 N, the hydrogel skin reduced the pulling force by a factor of 15 (from 2.65 N to 0.18 N). As the normal force was increased from 2 N to 5 N, the force required to pull the same uncoated specimen at the same rate increased by 150%. Compared to this, the required force to pull the coated specimen increased by only 60%, which illustrates how effectively the self-lubricating hydrogel skin is capable of reducing the surface friction under the increased load.

According to various embodiments, in addition to providing an inner core 3 for overall enhanced pushability and support of the elongate body 2, one or more selective portion(s) of the elongate body 2 having ferromagnetic particles 6 incorporated therein may be fabricated so as to not include an inner core 3. In other words, for example, where it is desired to have a distal end portion 7 that is softer and more flexible/more manipulatable than the remainder of the elongate body 2 having the inner core 3 disposed thereon, the inner core 3 may be designed to extend up to but not through the distal end portion 7. As such, in this embodiment, the selected distal end portion 7 is composed of the ferromagnetic soft polymer composite only (i.e., it excludes the inner core 3) and, thus, is substantially softer and more flexible/more manipulatable than the remainder of the elongate body 2 which contains the inner core 3. The softer and hence more responsive distal end portion 7 enables creating multiple modes and degrees of bending depending on the direction and strength of the applied actuation field and the unconstrained (i.e., coreless) length of the magnetically active distal end portion 7.

Figure 8A:
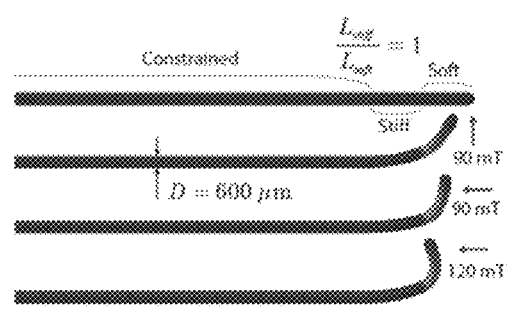
FIGS. 8A-D schematically illustrate simulations for quantitative prediction of multiple modes and degrees of bending of the soft continuum robotic devices according to embodiments of the invention, wherein a distal end portion of the elongate body is composed with no core, thus creating multiple modes and degrees of bending depending on the direction and strength of the applied actuation field and the unconstrained length of the magnetically active segment, with FIG. 8A showing an unconstrained length equal to that of the "soft" segment, such that only the very distal end tip of the strongly reacts to the applied magnetic fields, creating a J-shaped tip, FIGS. 8B-C showing that as the unconstrained portion becomes longer, the bending stiffness of the stiff segment decreases, increasing the radius of curvature of overall bending upon magnetic actuation, and FIG. 8D showing an experimental demonstration of navigating through a highly nonlinear path formed by a set of tightly spaced multiple rings, where the magnetic fields for actuation (20 to 80 mT) were generated by a cylindrical permanent magnet (diameter and height of 50 mm) at distance (from 40 to 80 mm) where the proximal end was pushed to advance the magnetically steered distal end of the device (having outer diameter 600 µm) during the navigation.
Figure 8B:
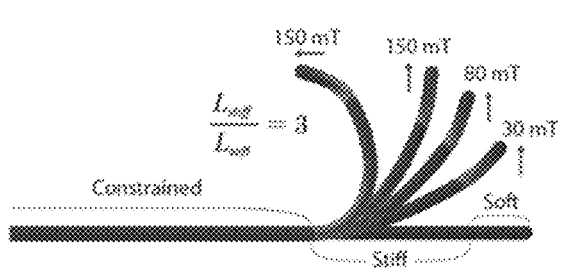
Figure 8C:
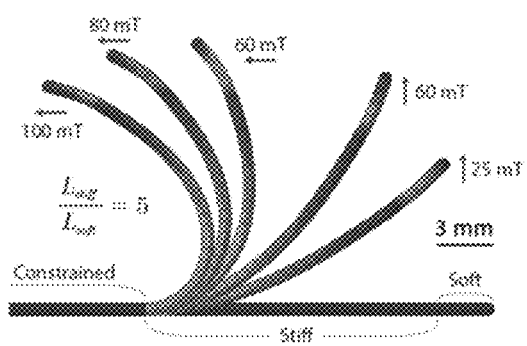

This is demonstrated in the simulation results presented in FIGS. 8A-D, when the unconstrained length of the stiff segment equals that of the soft segment, only the very end tip of the continuum robot strongly reacts to the applied magnetic fields, creating a J-shaped tip (FIG. 8A). This is because the short unconstrained segment has large bending stiffness. As the unconstrained part becomes longer, the bending stiffness of the stiff segment decreases, increasing the radius of curvature of overall bending upon magnetic actuation (FIGS. 8A-C). This multiple modes capability and degrees of bending enables the soft continuum robotic device 1 to make sharp turns and hence navigate through a highly nonlinear, tortuous path, as demonstrated in FIG. 8D where the tortuous path is created by a series of closely spaced rings.

In addition, by providing a distal end portion 7 that is substantially softer and more flexible than the remainder of the elongate body 2, the device will further minimize any damage, such as puncture or rupture, to internal structures that it comes into contact with (e.g., internal walls of blood vessels).

Suitable fabrication methods for the present invention soft continuum robotic device 1 may be chosen depending on the type of material (e.g., type of soft polymer matrix) used in forming the outer shell 4 of the elongate body 2.

According to various embodiments, conventional extrusion processes, which are used in forming commercial guidewires having polymer jackets and core wires, could suitably be used. In this conventional process, thermoplastic polymers (e.g. TPU) are heated and mixed with metallic powder (e.g. tungsten; for radiopacity to make the body visible under X-ray). This polymer melt mixture is then extruded around a core wire into a water bath for immediate cooling. Upon cooling, the TPU quickly solidifies. In order to form the present invention device 1, the selected outer shell 3 material is provided and mixed with the magnetic particles 6 at the desired concentration(s).

Further exemplary fabrication methods are depicted in FIG. 7. For example, a conventional extrusion processes (FIG. 7A(i)) used for guidewire jacketing can be suitably used for forming an elongate body 2 (particularly the outer shell 4 portion) out of thermoplastic polymers while forming the concentric inner core 3 therein. Other extrusion-based processes, such as 3D printing (FIG. 7B(i)) can be suitably used for forming an elongate body 2 (particularly the outer shell portion 4) out of both thermoplastic polymers as well as silicone-based ferromagnetic soft composite materials.

Figure 7A:
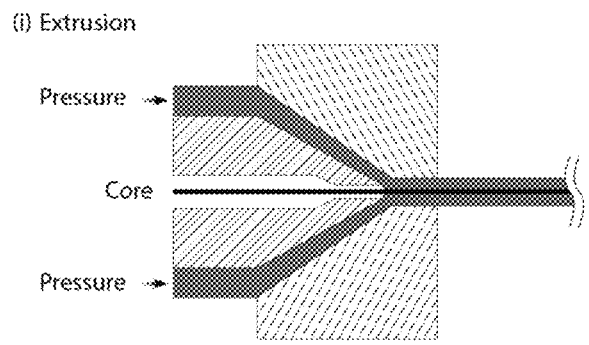
FIGS. 7A-D schematically illustrates fabrication methods for embodiments of the present invention soft continuum robotic device, with FIG. 7A showing a conventional extrusion process commonly used for jacketing thermoplastic polymers around a core, FIG. 7B(i) showing an extrusion-based printing method for fabricating an elongate body without an inner core, FIG. 7B(ii) showing injection molding to incorporate an inner core by injecting a ferromagnetic composite ink into a mold while placing the concentric core inside the mold, FIG. 7C illustrating a ferromagnetic composite ink based on PDMS+NdFeB (20 vol %) before and after magnetization, and FIG. 7D illustrating hydrogel skin formation onto the outer surface of a ferromagnetic soft continuum robotic device.
Figure 7B:
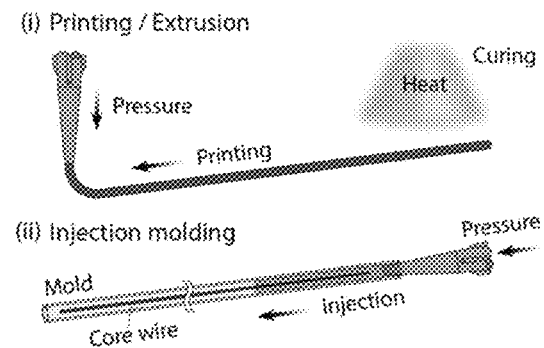

According to an exemplary embodiment, in a 3D printing process, uncured ferromagnetic composite ink consisting of silicone elastomer resin mixed with ferromagnetic particles 6 (or other suitable soft polymer matrix material with incorporated ferromagnetic particles 6) is used to form an overall elongate body member 2 (FIG. 7B(i)). As depicted, the formed structure does not incorporate the inner core 3. To fabricate an elongate body which incorporates a functional inner core 3, FIG. 7B(ii) shows an injection molding process in which a micro-mold in a cylindrical tube shape can be used to form the inner core 3. In particular, the ferromagnetic composite ink forming the outer shell 4 is injected while placing the concentric core inside the mold.

Figure 7C:
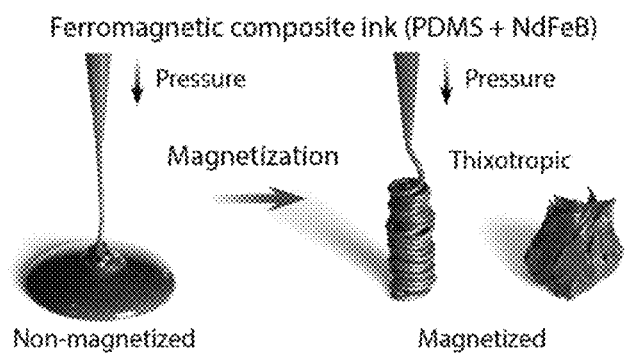
Figure 7D:
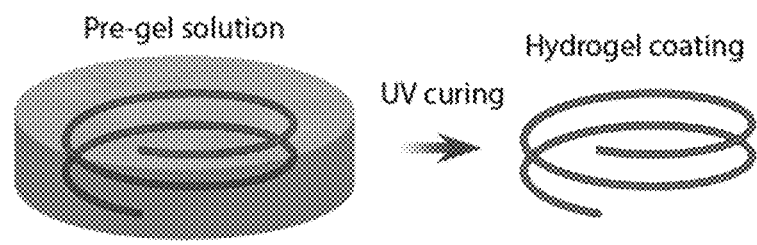

More specifically, according to various embodiments, the elongate body 2 may include one or more magnetically responsive portions, such as distal end portion, followed by a magnetically inactive segment (FIGS. 8A-C, 9A). The device can be fabricated as such by either printing or injection molding, both of which require extruding the thixotropic paste-like ink through a micro-nozzle by applying pressure (FIG. 7B). The printing technique differs from conventional extrusion of molten thermoplastic polymers in a sense that it does not require any heating to melt and fluidize the ink. The shear-thinning behavior of the magnetized ink ensures that the composite ink can be easily extruded when pressurized, while the presence of yield stress helps the deposited ink maintain its shape instead of spreading and becoming flat (FIG. 7C). To provide additional mechanical support or functionalities in the elongate body 2, an inner core 3 is incorporated into the elongate body (at the desired locations) through injection molding. For this process, a micro-tube is used as a mold, into which the thixotropic composite ink is injected while locating a concentric functional core inside the mold. Once the printing or injection is complete, the printed or molded ink undergoes thermal curing (PDMS-based composite) or solvent evaporation (TPU-based composite) upon heating to solidify into the elongate body 2. During the heating process, the presence of yield stress may help the unsolidified ink maintain its shape on the printing substrate or remain stable in the mold instead of flowing and escaping due to the decrease in viscosity at the elevated temperature. Thereafter, the magnetically active portion(s) are uniformly magnetized again, along the axial direction to possess programmed magnetic polarities required to create deflection upon magnetic actuation (FIGS. 5A-B).

According to various embodiments, more complex patterns of magnetic polarities, other than uniform magnetization along the axial direction, can also be programmed depending on the functional requirements of the soft continuum robotic device 1. As an example, an alternating pattern of magnetic polarities can be programmed to create wavy shape under applied magnetic fields. Such nonuniform magnetization pattern can be realized by several different methods. First, while printing the ferromagnetic composite ink to fabricate the elongate body 2 outer shell portion 4, magnetic fields can be applied around the printing nozzle to make the embedded ferromagnetic particles 6 reorient along the applied field directions. Second, after the fabrication of the elongate body 2 is complete, the elongate body 2 can be first deformed into a certain desired shape, and then a strong impulse magnetic field can be applied to permanently magnetize (or magnetically saturate) the embedded ferromagnetic particles 6 to achieve a desired nonuniform magnetization profile.

Figure 13A:
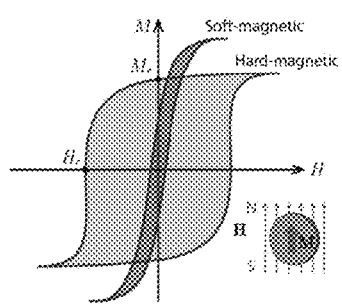
FIGS. 13A-F illustrate the rheological properties of ferromagnetic composite inks, with FIG. 13A showing magnetization curves with magnetic hysteresis loops of soft-magnetic and hard-magnetic materials, both of which develop strong induced magnetization M when exposed to an external magnetizing field $H_c$ with soft-magnetic materials forming a sharp and narrow hysteresis curve due to the low coercivity (and hence do not sustain high remnant magnetization $M_r$, independently of external fields) and with hard-magnetic materials exhibiting much higher coercivity (retaining high remnant magnetization unless a strong demagnetizing field beyond the coercivity is applied).

Ferromagnetic materials in general develop strong induced magnetization under applied magnetic fields. Unlike soft-magnetic materials, such as pure iron, which easily lose the induced magnetization once the external field is removed, hard-magnetic materials, such as neodymium-iron-boron (NdFeB), are characterized by their ability to retain high remnant magnetization against the external field once they are magnetically saturated due to their high coercivity (FIG. 13A). The main body of the soft continuum robotic device 1 is made of an elastomer composite that contains magnetizable microparticles (5-μm-sized on average; FIG. 14C) of NdFeB. The soft polymer matrix of the robot's body is composed of either silicone (polydimethylsiloxane; PDMS) or thermoplastic polyurethane (TPU) elastomers, depending on desired mechanical properties.

As the initial step of the fabrication process, the ferromagnetic composite ink is prepared by homogeneously mixing nonmagnetized NdFeB particles with an average size of 5 (or other desired ferromagnetic particles) with uncured PDMS resin or TPU dissolved (5 wt %) in solvent (N,N-dimethylformamide) (or other suitable soft polymeric matrix material) at a desired volume fraction (e.g using a planetary mixer such as AR-100, Thinky, at 2,000 r.p.m. for 2 min). For PDMS based ink, 5 wt % of curing agent containing platinum catalyst was added in the subsequent mixing for 45 sec under the same condition, after cooling down at room temperature for 1 min. To impart desired rheological properties to the mixture for ease of fabrication later, the whole mixture was magnetized by applying a strong impulse of magnetic fields to magnetically saturate the dispersed NdFeB particles. For example, using impulse magnetic fields (about 2.7 T) generated by an impulse magnetizer (IM-10-30, ASC Scientific).

Figure 13B:
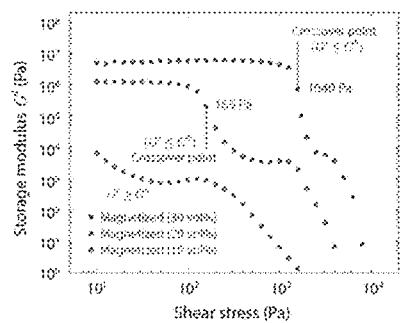
Figure 13C:
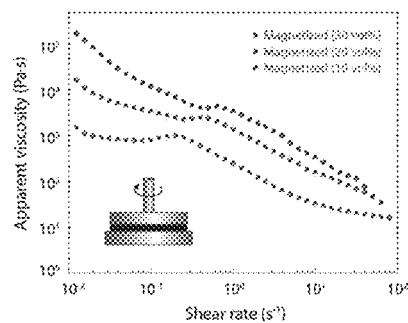
Figure 13D:
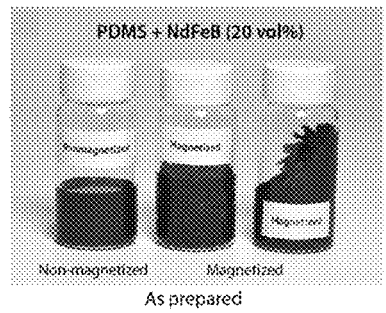
Figure 13E:
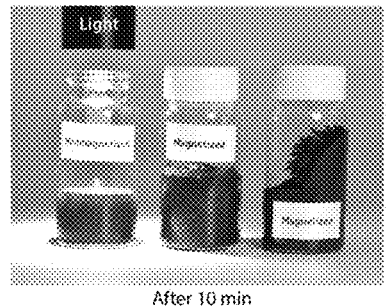
Figure 13F:
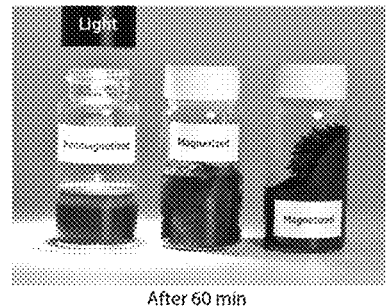

This turns the previously freely flowing mixture into a thixotropic paste (FIG. 7C) with shear-yielding (FIG. 13B) and shear-thinning (FIG. 13C) properties due to the strong interaction between the permanently magnetized NdFeB microparticles. The acquired rheological properties after magnetization are important fabrication, as detailed in the following section, but also conducive to preventing phase separation of the composite ink due to sedimentation of the dispersed particles over time (FIGS. 13D-F). The suppressed phase separation provides microstructural uniformity (FIG. 14B), which assumes formation of a homogeneous continuum when modeling the macroscopic behavior of the material to quantitatively predict the response of the present invention soft continuum robotic device 1 upon magnetic actuation.

According to embodiments of the present invention, a control mechanism in the form of a robotic manipulation platform may be used to generate magnetic fields required to actuate and control the soft continuum robotic device 1.

Figure 4A:
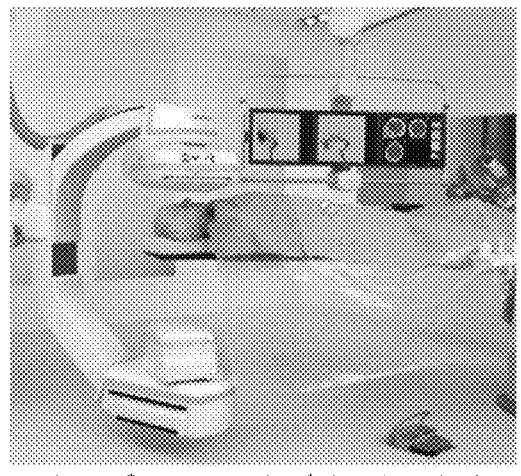
FIGS. 4B-D schematically illustrate a telerobotic manipulation platform for magnetic actuation and control of the present invention device according to an embodiment of the present invention, with FIG. 4A depicting a standard C-arm fluoroscope for real-time imaging of a patient's blood vessels based on continuous X-ray, FIG. 4B illustrating a 7-DOF (degrees of freedom) robotic arm holding a large cylindrical magnet used to apply and control the actuating magnetic fields and field gradients for magnetic actuation and steering of the present invention device based on a permanent magnet according to an embodiment of the present invention, where the magnet is aligned along a desired direction to induce the bending actuation on the soft continuum robotic device's magnetically responsive tip along the desired direction, wherein the degree of bending as determined by the applied field strength is controlled by adjusting the distance between the magnet and the steerable tip by remotely controlling the robot arm with any conventional controller mechanism (e.g. a joystick controller), with which an operator can advance/retract the guidewire and microcatheter under visual feedback from real-time imaging, FIG. 4C illustrating the robot arm deployed and used in the operating room along with a C-arm fluoroscope, FIG. 4D illustrating real-time teleoperation of the robot arm to control the position and orientation of the magnet with a joystick controller, and FIG. 4E illustrating the magnetically steerable soft continuum robotic guidewire steered by the magnet held by the robot arm to navigate through the neurovascular phantom.
Figure 4C:
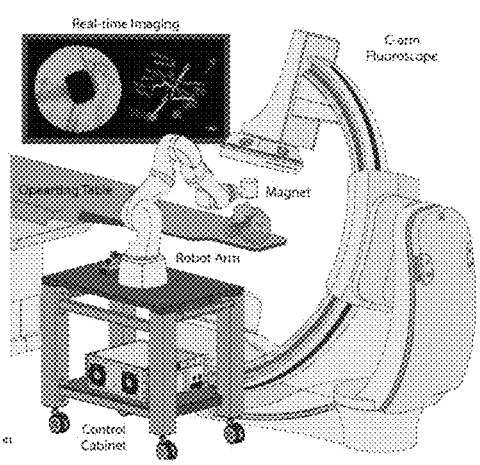
Figure 4B:
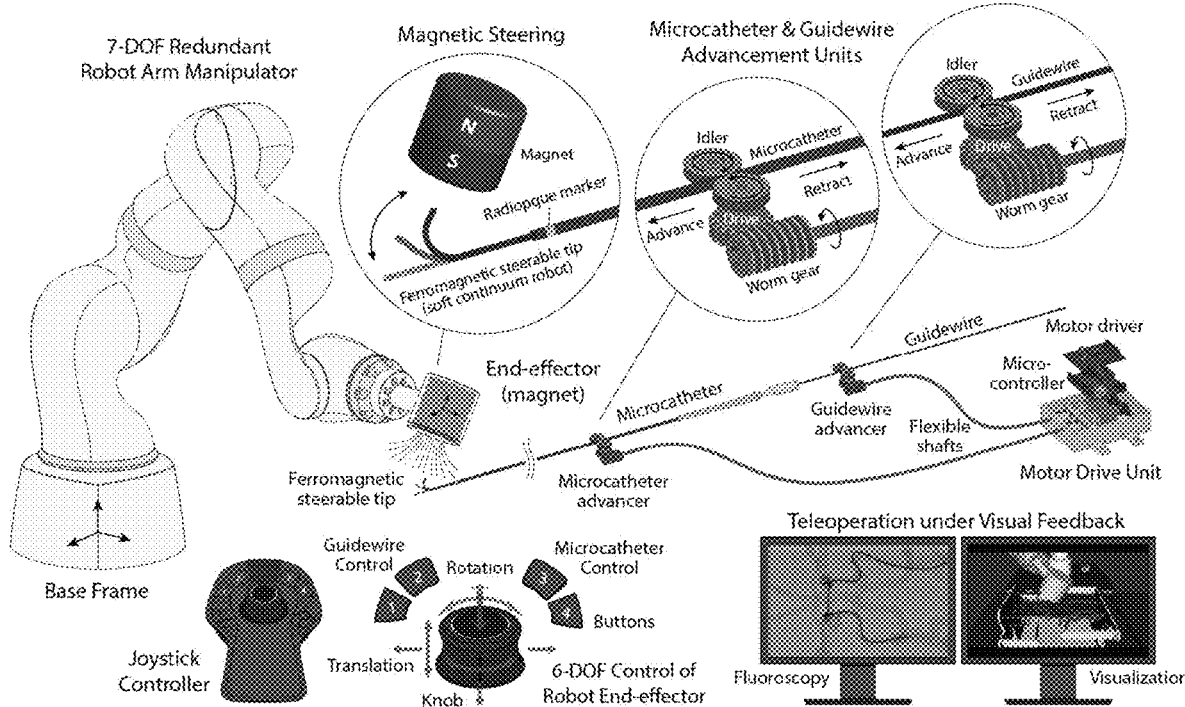
Figure 4D:
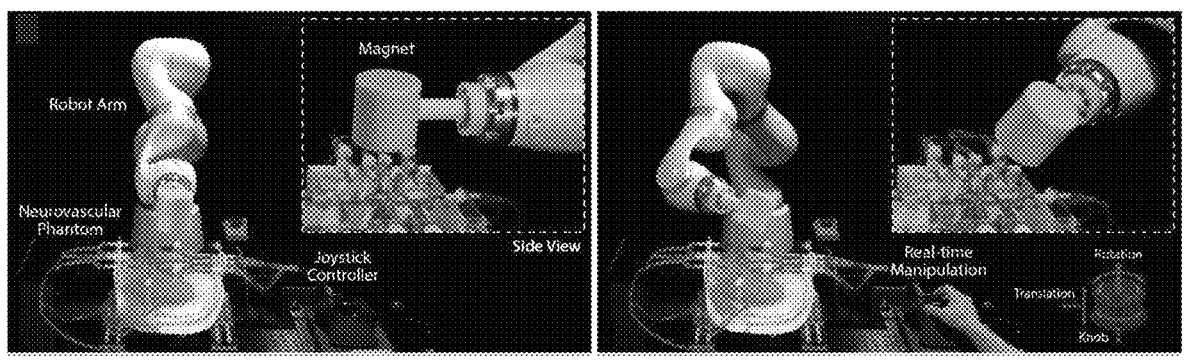
Figure 4E:
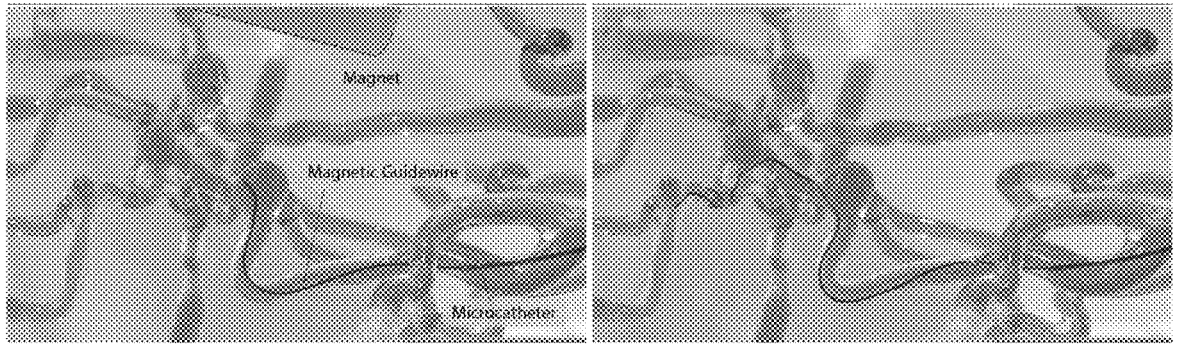

According to an embodiment of the present invention, the soft continuum robotic device 1 is controlled through a control mechanism in the form of a single permanent magnet held and manipulated by a multi-degree of freedom (DOF) robotic arm. For example, a 7-DOF robotic arm holing a large permanent magnet can be configured to control the steering amount and direction by varying the applied field strength and direction. A motorized device to precisely insert and advance the soft continuum robotic device 1, from its proximal end upon remote control at the workstation console, may also be provided to enable teleoperation. One exemplary embodiment of this type of control mechanism is depicted in FIGS. 4B-C. The control mechanism is both compact and efficient mechanisms of generating and control magnetic fields for actuating the magnetically steerable soft continuum robotic device 1. In particular, the single permanent magnet and robotic arm are configured and arranged such that changing the orientation and distance of the magnet relative to the soft continuum robotic device 1, results in modifications to the direction and strength of the applied magnetic field. Thus, a human operator can remotely control (e.g., teleoperate) the robotic arm. According to embodiments of the invention, standard fluoroscopic imaging, which visualizes radiopaque components or markers (such as gold or tungsten) of guidewires/catheters, will be directly applicable by incorporating in the soft continuum robotic device 1 a sufficient volume of radiopaque magnetic particles that are visible under X-ray. In these embodiments, the present system can be integrated with a standard C-arm fluoroscope (e.g., FIG. 4C) or other suitable mechanism to enable observation of the state of the soft continuum robotic device so that a surgeon can remotely manipulate the device while receiving real-time visual feedback in the control of the robotic arm.

According to alternate embodiments, commercialized magnetic manipulation systems based on (i) a pair of large magnets controlled by robotic arms such as Stereotaxis Niobe® or Genesis' or (ii) multiaxial electromagnetic coils such as Magnetecs CGCI or Aeon Phocus may be adopted for use with the present invention soft continuum robotic device 1.

According to an embodiment of the present invention, the capability of the present invention ferromagnetic soft continuum robotic device 1 to navigate complex and constrained environments is demonstrated. Such navigation is based upon active steering using magnetic actuation in combination with the ferromagnetic particles 6 dispersed within the outer shell 4. In addition, further functionalities (laser delivery, imaging, illumination, CMOS sensing, etc) may be enabled by incorporating a functional inner core 3 (e.g., one or a bundle of optical fibers)

FIGS. 9A-B illustrate an embodiment of the device passing through a set of rings using the magnetically responsive distal end portion 7, which follows the direction in which the actuating field is applied. For experimental demonstration, a cylindrical permanent magnet (diameter and height of 50 mm) was employed to apply the actuating magnetic fields at distance. The basic principle for magnetic actuation and steering is to align the central axis (denoted z-axis in FIG. 18A) of the magnet along the desired direction to induce bending of the device distal end portion 7 towards the desired direction (FIG. 18B). Although the bending actuation in general is driven by magnetic body torques as discussed earlier, the spatial gradients of applied magnetic fields can also give rise to magnetic body forces, which further encourage the device's distal end portion 7 to align itself along the magnet's central axis (FIG. 19), as discussed in the Supplementary Text at the end of the disclosure.

Figure 17A:
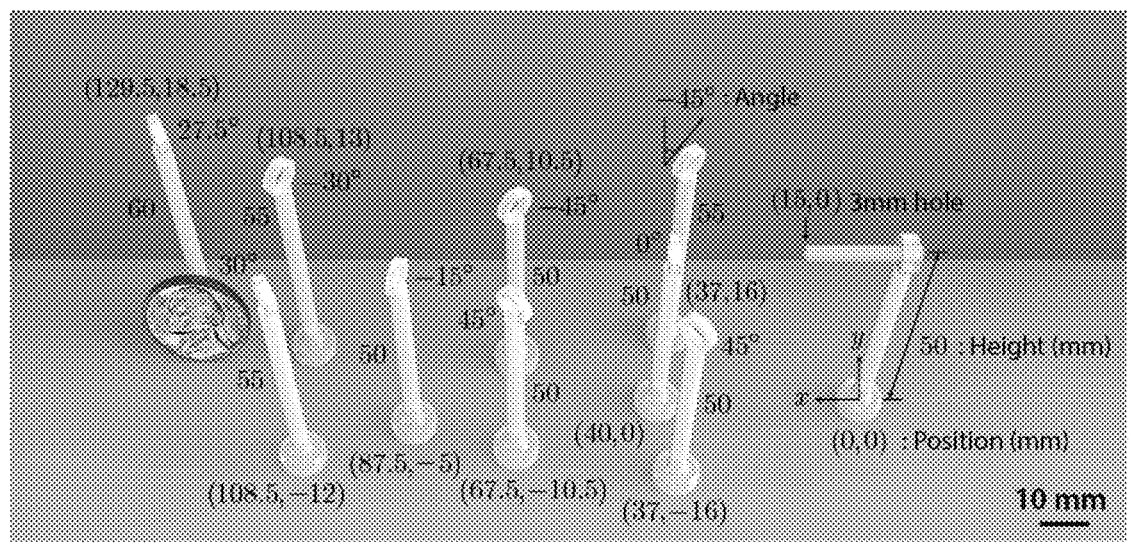
FIGS. 17A-B show experimental setups and dimensions for the demonstrations of active steering and navigating capabilities of ferromagnetic soft continuum robotic devices according to embodiments of the present invention, based on magnetic actuation, where

FIG. 9B shows an experimental demonstration of the fabricated prototype, which selectively navigates through a set of loosely placed rings (see FIG. 17A for details) based on magnetic actuation and steering achieved by manually manipulating a single magnet. The demonstrated prototype was fabricated through injection molding (FIG. 7B) of a PDMS+NdFeB composite ink being 600 μm in diameter. To provide mechanical support and pushability, a nickel-titanium alloy (nitinol) core was incorporated (FIG. 9A) in the robot's body. Since the nitinol core was from the tip of a commercial guidewire, the magnetically responsive tip is naturally connected to the commercial guidewire (see Materials and Methods below for details). The navigating performance of the prototypes showed an average time taken to complete the demonstrated task: 50±1.58 sec.

Figure 8D:
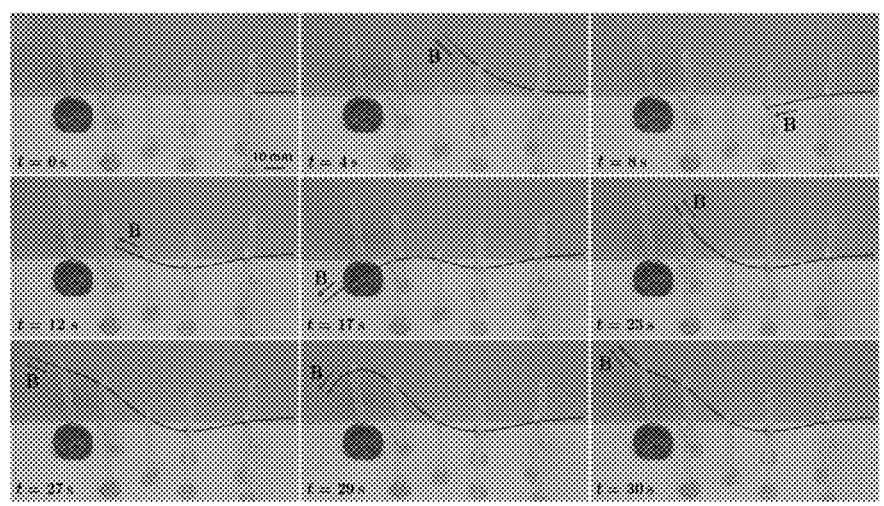
Figure 16E:
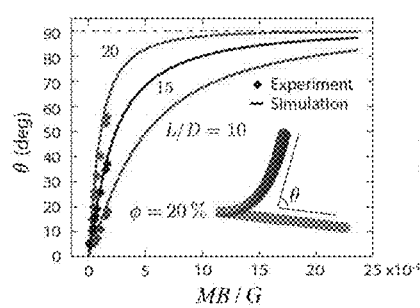
Figure 17B:
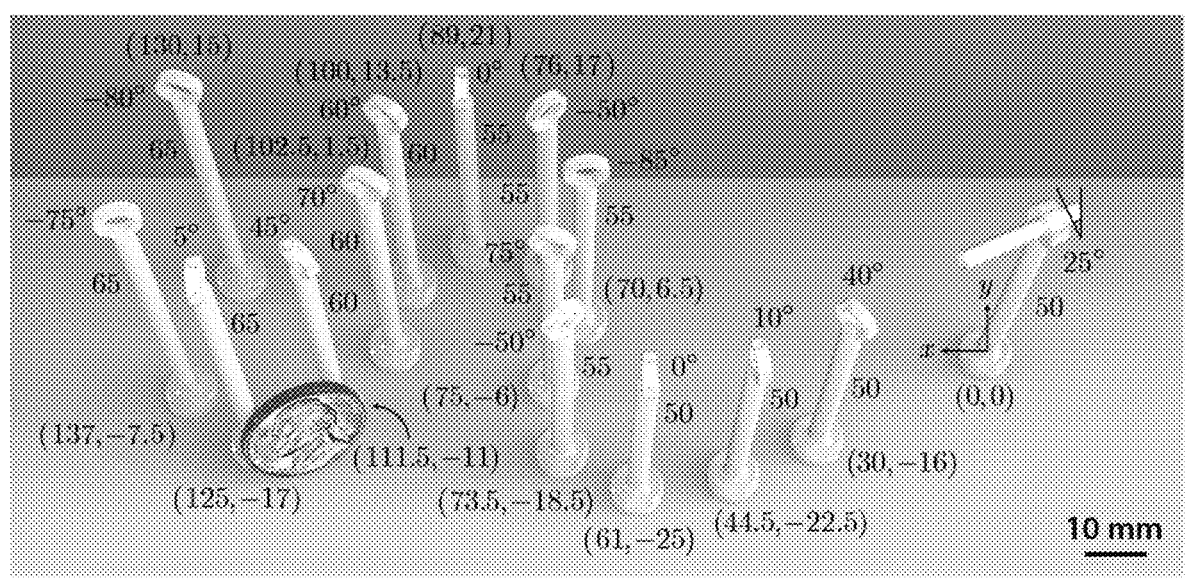

To enable making sharp turns and hence navigating through a tortuous path, a variation in the bending stiffness of the magnetically responsive portion(s) of the soft continuum robotic device 1 was introduced. The resulting continuum robotic device 1 (diameter of 600 μm) had a short (3-mm long), softer segment at the distal end of the magnetically active portion. This softer segment was composed of the PDMS+NdFeB composite only (no inner core 3) and, thus, was substantially softer than the remainder which contained the stiff nitinol inner core 3 (diameter of 80 μm). The effective Young's modulus of the stiffer segment (14 MPa) was calculated to be 10 times that of the softer segment (1.4 MPa) from Eq. (5) in Materials and Methods section. Both segments had uniform magnetization (M=128 kA/m) along the axial direction. The softer and hence more responsive tip enables creating multiple modes and degrees of bending depending on the direction and strength of the applied actuating field, as well as the unconstrained length of the magnetically active segment, as predicted from the model-based simulation in FIGS. 8A-C. When the unconstrained length of the stiff segment equals that of the soft segment, only the very end tip of the continuum robotic device 1 reacts effectively to the applied magnetic fields, creating a J-shaped tip (FIG. 8A). This is because the short unconstrained segment has a large bending stiffness due to the small aspect ratio, as predicted in FIG. 16E. As the unconstrained length increases, the bending stiffness of the stiffer segment decreases, which increases the radius of curvature of overall bending upon magnetic actuation (FIG. 8B-C). FIG. 8D shows the experimental demonstration of our fabricated prototype navigating through a tortuous path formed by a series of tightly spaced rings (see FIG. 17B for details) based on the ability to make sharp turns, which is enabled by the unique design of the present invention device 1.

Figure 2A:
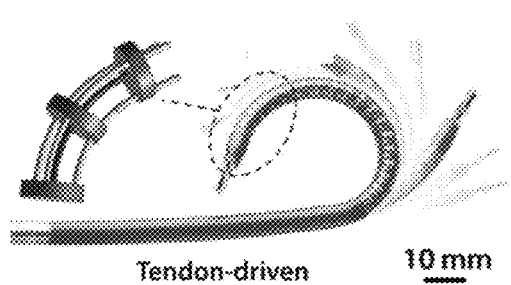
FIGS. 2A-J schematically illustrate the challenges in existing continuum robots and steerable robotic catheters, with FIG. 2A depicting tendon-driven continuum robots based on pulling/pushing antagonistic pairs of mechanical wires for applications in cardiac electrophysiology, FIG. 2B depicting magnetically steerable continuum robots having a series of permanent magnets embedded in the distal tip of the device, FIG. 2C showing the considerably smaller and more tortuous vascular structures involved in the cerebrovascular anatomy, FIG. 2D showing that the internal carotid arteries which are smaller than 5 mm in diameter, and the cerebral arteries which are typically smaller than 2.5 mm in diameter, FIGS. 2E-F showing a steerable sheath (Magellan™ of Hansen Medical) driven by mechanical wires to steer a conventional guidewire, which can be advanced/retracted or rotated by the linear/rotary drive from the proximal end, FIG. 2G showing a magnetically controlled catheter, with several rigid magnets embedded in the distal segment, used for cardiac electrophysiology to treat heart arrhythmia (Stereotaxis Inc.), FIGS. 2H-I showing a Corpath® GRX of Corindus Vascular Robotics to advance/retract or rotate a conventional passive guidewire with a linear/rotary drive from the proximal end, and FIG. 2J showing a magnet-tipped microguidewire with a finite-sized rigid magnet attached at the distal end tip, which is thicker than the guidewire.
Figure 2B:
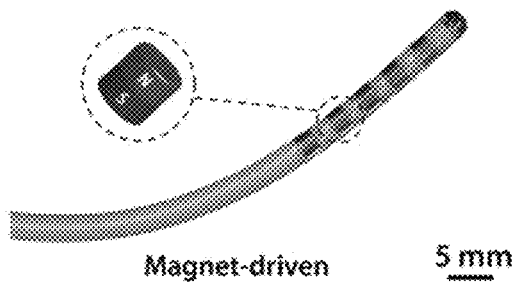
Figure 2C:
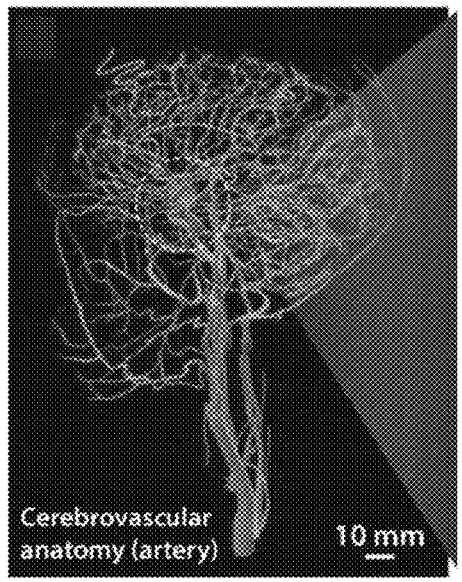
Figure 2D:
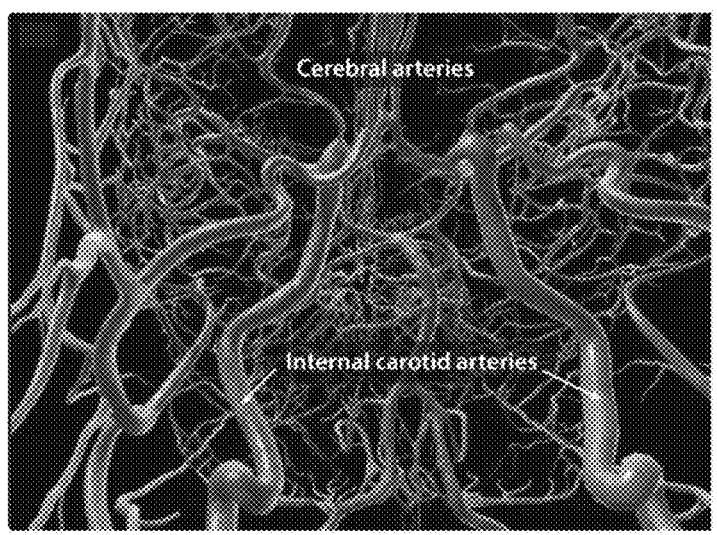
Figure 2E:
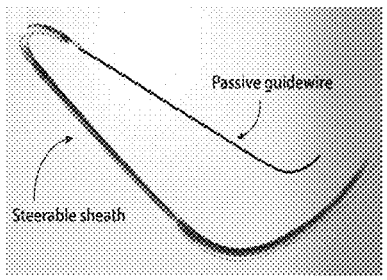
Figure 2F:
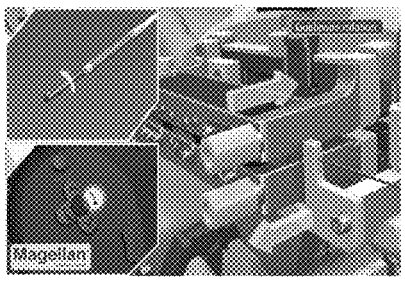
Figure 2G:
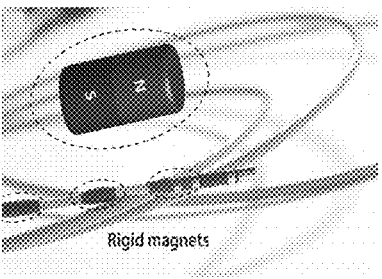
Figure 2H:
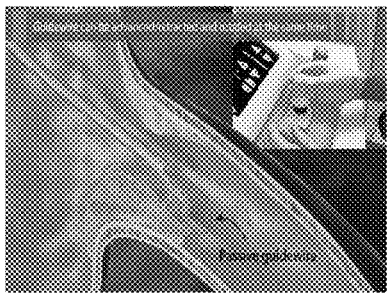
Figure 2I:
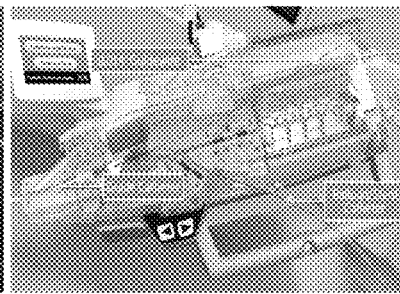
Figure 2J:
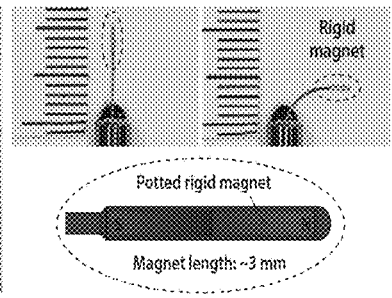
Figure 10A:
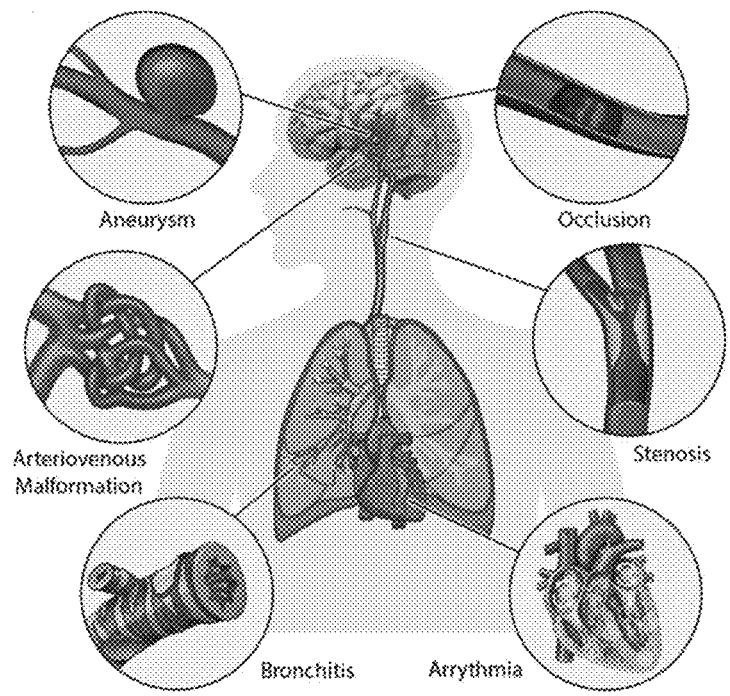
FIGS. 10A-B schematically illustrate pathologic conditions in hard-to-reach areas across the human body (FIG. A), with FIG. 10B illustrating a soft continuum robotic device according to an embodiment of the present invention navigating through a complex neurovasculature with an aneurysm based on magnetic actuation.
Figure 10B:
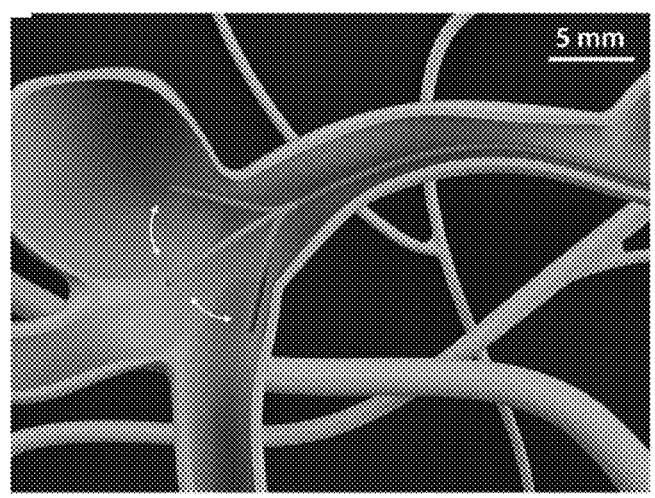

In order to provide highly adaptable and smooth navigation through nonlinear branches of the vasculature, such as the cerebrovasculature (see FIG. 2C-D) which includes very narrow and acute-angled corners, the present invention provides a soft continuum robotic device 1 having omnidirectional steerability based on tether-free actuation mechanisms as well as sufficient mechanical rigidity and pushability (i.e., when advancing the device through the vasculature, the proximal part is pushed to advance the device forward as a whole). The designed soft continuum robotic device 1 may open new avenues to teleoperated, minimally invasive robotic surgery for previously inaccessible lesions or difficult-to-reach areas across the human body (e.g., FIGS. 10A-B), thereby addressing challenges and unmet needs in healthcare. Potential applications of such multifunctional soft continuum robots include laser-assisted treatment of vascular occlusion (blockage due to a thrombus) or atherosclerosis (narrowing due to plaque buildup), so-called laser atherectomy. In addition, the device 1 may further be equipped with a miniature CMOS sensor, while having multiple functional cores for both illumination and imaging. As such, the soft continuum robotic device 1 may further enable submillimeter-scale endoscopic procedures such as angioscopy to better diagnose pathologic conditions such as embolism or aneurysms in the affected sites of intracranial arteries, which is far less accessible due to the considerably small and tortuous vascular structures.

Figure 20A:
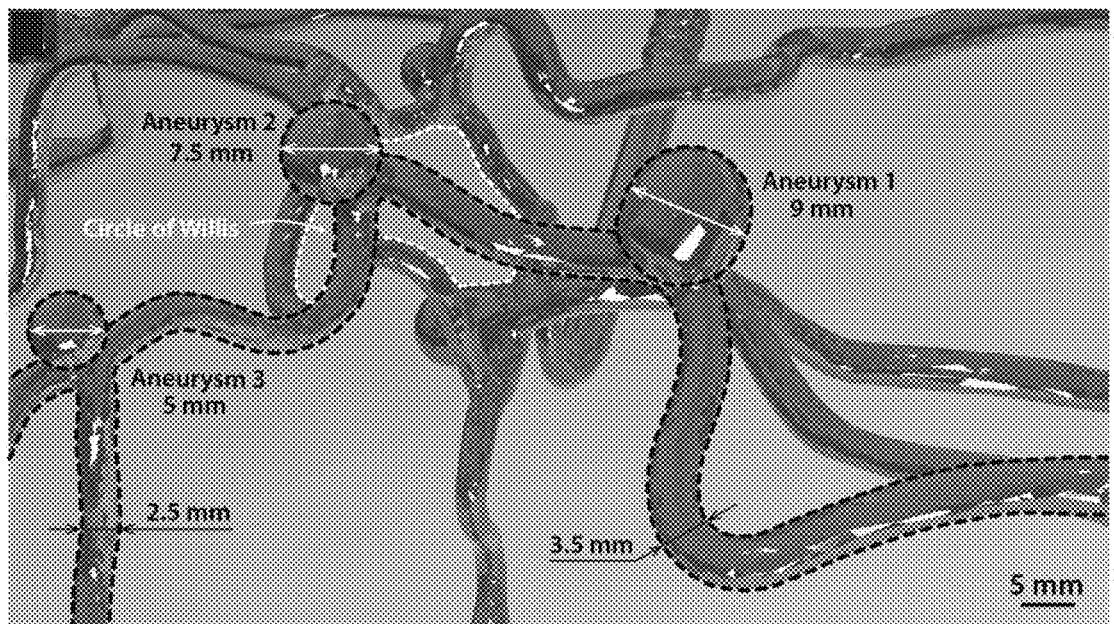
FIG. 20A-C depict dimensions and details of the cerebrovascular phantom model used for the experimental demonstration of the active steering and navigating capabilities of the present invention ferromagnetic soft continuum robotic device, where
Figure 20B:
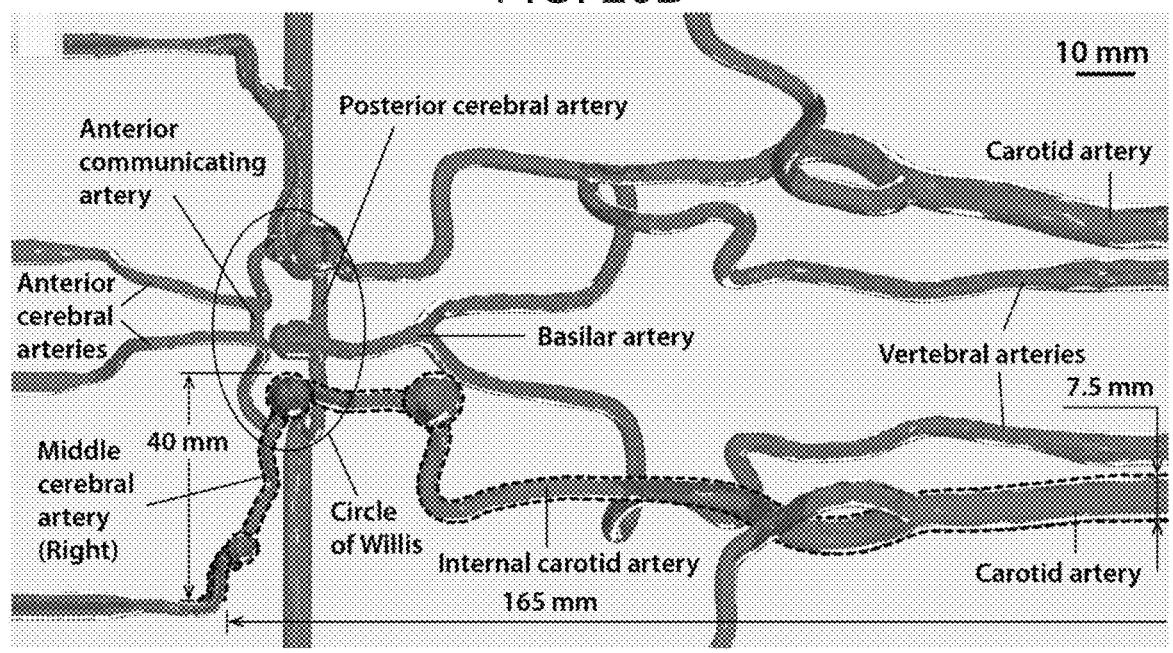
Figure 20C:
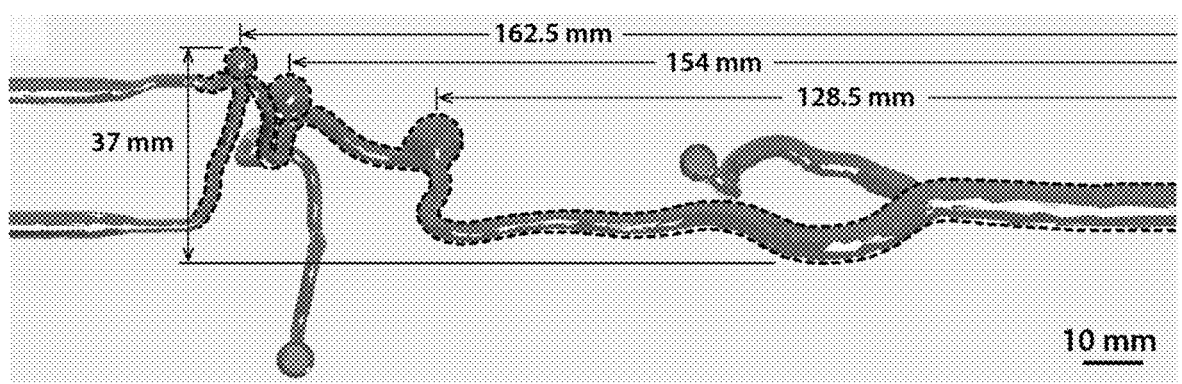

To illustrate the potential impacts in medical applications, the steering and navigating capabilities are demonstrated in realistic, clinically relevant environments (See FIGS. 11, 12 and 20A-C). In one demonstration, the soft continuum robotic device 1 was magnetically controlled to navigate through portions of a real-sized vascular phantom model (made of silicone) for a particular neurovasculature (the so-called the circle of Willis) with multiple aneurysms (localized dilation of a blood vessel) at different locations. Noticeably, as can be seen in FIGS. 20A-C, the vascular structures are highly complex and tortuous, involving several acute-angled corners. As depicted in greater detail (FIGS. 20A-C), the inner diameter of the silicone vessels along the targeted path (from carotid artery to middle cerebral artery FIG. 20B) to be navigated by the soft continuum robotic device 1 ranged from 2.5 to 7.5 mm, while the sizes of the aneurysms to reach along the path were 9 mm (first), 7.5 mm (second), and 5 mm (third) in diameter, respectively (FIG. 20A). The overall distance navigated by the robotic device 1 along the targeted path was around 250 mm (FIGS. 20B-C)). The required task for the present invention ferromagnetic soft continuum robotic device 1 was to reach all the aneurysms along the targeted path, while at the same time demonstrating the ability to locate the elongate body's 2 distal tip inside each aneurysm based on magnetic actuation and steering capabilities. In addition, direct contact of the elongate body 2 with the inner wall of the aneurysms should be avoided, given the fact that the aneurysms have high risk of rupture, which can lead to hemorrhagic stroke. The present invention ferromagnetic soft continuum robotic device 1 was demonstrated to successfully carry out the required tasks in the vascular phantom, which was filled with a blood analogue that simulated the friction between commercial guidewires and real blood vessels. Ferromagnetic soft continuum robotic devices 1 with and without a self-lubricating hydrogel skin were both tested, with the device including the hydrogel skin substantially reducing the friction acting on the device while going through the first acute-angled corner, thus preventing unwanted jerky movement of the device.

Among the series of tasks described above, manually controlled passive guidewires with pre-bent tips may somewhat easily pass the first sharp corner and follow the constrained path, owing to their highly passive and compliant nature. At the second sharp corner next to the first aneurysm, however, there is no continuous path that is narrow enough to effectively constrain and guide the passive wire because of the large empty space within the aneurysm. In this scenario, in the presence of such acute angulation in particular, the J-shaped tip becomes no longer useful due to the limited range the tip can cover. When pushed further, the tip of the passive wire will unavoidably scratch the inner wall of the aneurysm, as the wire coils up and travels along the spherical inner surface while applying unnecessary pressure on the wall. This poses a high risk of aneurysm rupture, which can lead to hemorrhagic stroke if the aneurysm were located in in the cerebral vasculature.

Due largely to these functional limitations inherent in manually controlled guidewires, it is quite challenging and complex to navigate such aneurysms with acute angulation with manual devices even after multiple reshaping maneuvers to adjust the shape of the tip. As such, the demonstrated capabilities of the present invention soft continuum robotic device 1 to navigate through acute, highly nonlinear branches of neurovasculature will facilitate endovascular procedures by enabling the access to difficult-to-reach areas.

Further extending the capabilities of the present invention ferromagnetic soft continuum robotic device 1, additional functionalities enabled by a functional core were further demonstrated. As an illustrative example, an optical fiber was incorporated in the elongate body 2 as the inner core 3 to demonstrate magnetically steerable laser delivery (FIGS. 6A-B). In the experimental settings for the demonstration, the fabricated soft continuum robotic device 1 outer diameter was designed to be 500 µm. The incorporated optical fiber had an outer diameter of 245 µm and comprised a silica core, cladding, and protective acrylate coating. The given task was to accurately point at the small targets (2-mm dots) with the laser beam in a desired order based on the magnetic actuation (FIG. 6B). The omnidirectional steering and the flexible motion allowed the soft continuum robotic device 1 to successfully carry out the desired task.

Figure 12A:
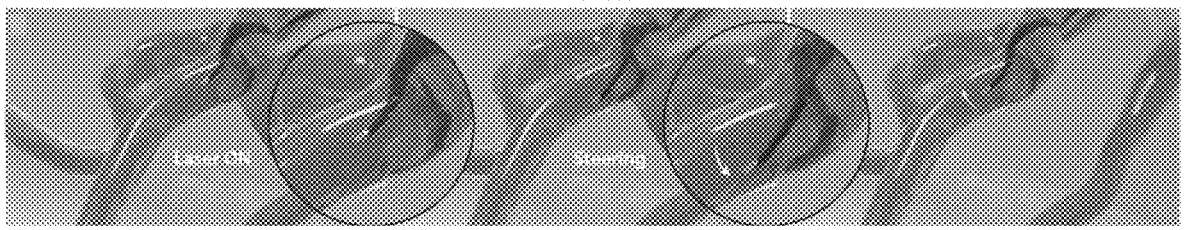
FIG. 12A-B illustrate a demonstration of steerable laser delivery in realistic environments, where
Figure 12B:
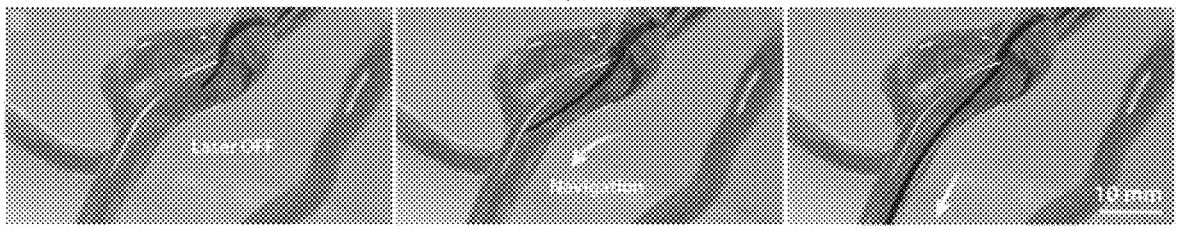

One potential medical applications of the demonstrated capabilities in FIG. 6 is the laser-assisted treatment of vascular stenosis (or atherosclerosis; narrowing of an artery due to plaque buildup on the inner walls), which commonly occurs in the carotid artery, through which the blood is supplied from the heart to the brain. As demonstrated within this context, the present invention soft continuum robotic device 1 having an incorporated laser-delivering functional inner core 3 was used in a carotid artery phantom (FIGS. 12A-B). In the demonstration, the device first reached the target site in the carotid artery and then emitted a laser beam near the inner wall. It then changed the direction and position of the laser-emitting tip using magnetic steering (FIG. 12A). After that, it turned off the laser and navigated downstream through the carotid artery (FIG. 12B).

The magnetic steerability and the resulting capability to keep the laser-emitting tip in position may help preventing unwanted movement or displacement of the tip from the desired location during laser ablation, thereby improving the accuracy and the safety, which are of paramount importance throughout the whole procedure.

By providing the present devices so as to include the above-described properties, patients undergoing a procedure will benefit from the reduced time and improved accuracy thus provided, while surgeons will also benefit from the reduced fatigue and the ability to work away from the radiation source required for real-time imaging during the intervention. Further, the present device and method will provide new avenues to telerobotic endovascular neurosurgery to enable early intervention of acute ischemic stroke, thereby addressing the current key challenges and unmet needs in healthcare.

Materials and Methods

In the various prototypes and examples, the following materials and methods were used unless otherwise noted.

Ferromagnetic Composite Ink Preparation

The ferromagnetic composite ink was prepared by homogeneously mixing NdFeB microparticles with an average size of 5 μm (MQFP-B-2007609-089, Magnequench) into uncured PDMS resin (Sylgard 184, Dow Corning) or TPU (Elastollan Soft 35A 12P, BASF) dissolved (50 wt %) in N,N-dimethylformamide (Sigma Aldrich) at prescribed volume fraction using a planetary mixer (AR-100, Thinky) at 2,000 r.p.m. for 2 min. For PDMS-based ink, 5 wt % of curing agent containing platinum catalyst was added in the subsequent mixing for 45 sec under the same condition, after cooling down at room temperature for 1 min. The mixture was then magnetized by impulse magnetic fields (about 2.7 T) generated by an impulse magnetizer (IM-10-30, ASC Scientific) to impart magnetic polarities to the NdFeB particles embedded in the unsolidified elastomer resin.

Magnetic Characterization

The magnetic moment densities of ferromagnetic soft composites based on PDMS+NdFeB with different particle concentrations were measured with a vibrating sample magnetometer (DMS 1660, ADE Technologies). Specimens were prepared from thin sheets of the composite materials obtained from molding by cutting them into 6-mm circles using a biopsy punch (Miltex Inc.) to fit into the sample holder of the magnetometer. The remnant magnetic moments of the samples were measured when the applied external field is zero, and then divided by the sample volume to obtain the magnetization, or magnetic moment density.

Mechanical Testing

Rectangular planar sheets (12 mm×35 mm×1 mm) of ferromagnetic soft composites based on PDMS+NdFeB with different particle concentrations were prepared by molding and then cut into dog-bone-shaped specimens with known dimensions (width 4 mm, gauge length 17 mm) for tensile testing. The specimens were tested on a mechanical testing machine (Z2.5, Zwick/Roell) with a 20-N load cell at a strain rate of $0.01 \text{ s}^{-1}$. Nominal stress-stretch curve was plotted for each specimen, and the shear modulus was identified by fitting the experimental curve to a neo-Hookean model. When compared with the particle-filled elastomers, hydrogels are orders of magnitude softer in terms of Young's modulus. Due to this significantly lower modulus, the hydrogel skin does not contribute to the bulk mechanical property of the coated specimen. Therefore, for simplicity, the mechanical properties of the ferromagnetic soft composites were measured from uncoated samples without hydrogel skins.

Silica Coating of Magnetic Particles

The NdFeB microparticles were coated with a layer of silica (SiO2) through hydrolysis and polycondensation of tetraethyl orthosilicate (TEOS; Sigma Aldrich), widely known as the Stober method, followed by the nucleation of the silica around the particle. First, 40 g of NdFeB microparticles were dispersed in 1,000 mL of ethanol while vigorously stirring to avoid sedimentation at 1,500 r.p.m using a digital mixer (Cole-Parmer). Then 60 mL of 29% ammonium hydroxide was slowly added to the mixture, followed by slow addition of 2 mL of TEOS. The mixture was stirred for 12 hr at room temperature and then washed with acetone multiple times after the reaction. The suspension was then vacuum-filtered to obtain the silica-coated particles.

Fabrication of Ferromagnetic Soft Continuum Robotic Devices

The TPU-based prototype demonstrated in FIG. 9B was fabricated by joining a printed segment to a commercial guidewire with a TPU jacket and a nitinol core. For the process, the prepared composite ink based on TPU+NdFeB (30 vol %) was first loaded into a syringe barrel and then mounted to the custom-designed 3D printer based on a Cartesian gantry system (AGS1000, Aerotech). A conical nozzle (outlet diameter of 838 μm, Smoothflow Tapered Tip, Nordson EFD) was used to extrude the inks by applying pressure. The printed TPU composite fiber was thermally welded to a commercial guidewire with a TPU jacket (ZIPwire™ Hydrophilic Guidewire; 810-μm diameter, Boston Scientific) using a heat-shrink tube (inner diameter of 1.02 mm; Nordson Medical), in which the two segments were placed and locally heated at 190° C. During the heating localized at the junction, the TPU composites of both segments partially melt and then join together when cooled down, creating a seamless connection of the two segments.

The ferromagnetic soft continuum robots with functional cores presented in FIGS. 6, 8, 9, 11 and 12 and were fabricated through injection molding, for which micro-tubes made of heat-resistant polymers such as polytetrafluoroethylene or polyimide (Nordson Medical) were used as molds. For the prototypes presented in FIGS. 8, 9 and 11, in which tapered nitinol cores were incorporated, commercial guidewire products (Headliner® Hydrophilic Guidewire; 300-μm diameter, Terumo) were used as templates. For a specified length of the commercial guidewire (25 cm from the distal tip), the TPU-based polymer jacket was first partially melt and stripped off by locally applying heat (250-300° C.) to expose the tapered nitinol wire (distal diameter of 80 μm). Then, the prepared ferromagnetic composite ink based on PDMS+NdFeB (20 vol %) was injected into the 610-μm polyimide micro-tube through a conical nozzle (outlet diameter of 120 μm) while placing the tapered nitinol wire inside the mold (FIG. 7B). After curing upon heating at 160-190° C. for 5 min, the mold tubing was stripped off with a razor blade to retrieve solidified body of the fabricated ferromagnetic soft continuum robot. For the prototype presented in FIGS. 6 and 12, a single-mode optical fiber (diameter of 245 μm including the 3-μm core, 125-μm cladding, and protective acrylic polymer coating; Thorlabs Inc.) was used as a functional core, followed by the same injection molding procedures with 510-μm polyimide mold described above.

After growing hydrogel skin on the outer surface (see below), all the demonstrated prototypes were uniformly magnetized along the axial direction by applying an impulse magnetic field (about 2.7 T) generated by an impulse magnetizer (IM-10-30, ASC Scientific) to magnetically saturate the embedded NdFeB particles.

Hydrogel Skin Formation

Following the previously reported protocol (Y. Yu, H. Yuk, G. A. Parada, Y. Wu, X. Liu, C. S. Nabzdyk, K. Youcef-Toumi, J. Zang, X. Zhao, *Multifunctional "hydrogel skins" on diverse polymers with arbitrary shapes*, Adv. Mater. 31, 1807101 (2019).), the uncoated samples were first cleaned with ethanol and isopropanol, followed by drying under nitrogen flow. To promote wettability of the uncoated polymer, the samples were treated with a plasma cleaner (PDC-001, Harrick Plasma) for 1.5 min. The plasma-treated samples were then immersed in an organic solution of ethanol containing 10 wt % benzophenone for 10-15 min. After removing excess solution on the surface with wipes, the samples were then immersed in a pre-gel solution containing 30 wt % hydrogel monomers (N,N-dimethylacrylamide; DMAA, Sigma Aldrich) and 1 wt % Irgacure-2959 (Sigma Aldrich) based on deionized water, which was degassed for 5 min before preparing the pre-gel solution. For UV curing, the pre-gel solution bath was subjected to UV irradiation (CL-1000, UVP) for 60 min. Then, unreacted regents were removed by rinsing with deionized water using an orbital shaker (Micro Plate Shaker, VWR) for 24 h. For imaging hydrogel skin (FIGS. 15A-D), both coated and uncoated samples (20 mm×20 mm×1 mm) based on PDMS+ NdFeB (20 vol %) prepared by molding were immersed in an aqueous fluorescein solution before imaging to visualize the hydrogel layer.

Friction Coefficient Measurement

For friction coefficient measurement, both coated and uncoated samples (20 mm×20 mm×1 mm) were prepared based on PDMS+NdFeB (20 vol %) composites. To quantify the friction coefficients, the torque required to shear the specimens at prescribed shear rates (from 0.1 to 1.0 s−1) under prescribed normal pressure (from 3 to 9 kPa) was measured from a rotational rheometer (AR-G2, TA Instruments) in normal force control mode with a 20-mm diameter steel plate geometry. Deionized water was smeared on top of both coated and uncoated surfaces before shearing the samples. The friction coefficients were calculated following the previously reported protocol (G. A. Parada, H. Yuk, X. Liu, A. J. Hsieh, X. Zhao, *Impermeable robust hydrogels via hybrid lamination*, Adv. Healthc. Mater. 6, 1700520 (2017).).

Pulling Test

For pulling test, a cylindrical geometry was adopted for relevance to the actual shape of the continuum robot. For ease of measurement, however, the pulling test was conducted with a large-scale prototype with 8-mm diameter. Both coated and uncoated sheets of PDMS+NdFeB (20 vol %) composites with 1-mm thickness were wrapped around a glass rod with silicone adhesives (Sil-Poxy, Smooth-On Inc.) applied for secure bonding. The normal force was applied by a pair of half-cylindrical grips made of PDMS, where the upper grip was connected to the load cell of a mechanical testing machine (Z2.5, Zwick/Roell) to apply the prescribed normal force (2 N or 5 N) to the specimen held between the grips. The specimens were pulled by a linear actuator equipped with a load cell at a constant speed (200 mm/min) while being immersed in a bath of deionized water. The load cell attached on the pulling grip measured the forces required to pull the specimens at the given speed.

Finite Element Analysis

For simulation results presented in FIGS. 8 and 16, a user-defined element subroutine was used with the commercial finite-element analysis software Abaqus. For parametric studies presented in FIGS. 16F, H and I, Eqs. (2) and (3) were implemented as input parameters for material properties. In all simulations, the bulk modulus was set to be 1,000 times the shear modulus to approximate the incompressibility, and the direction and strength of a uniform magnetic field were defined as additional input parameters. For simulating multiple modes and degrees of bending presented in FIG. 8A-C, the magnetization parameter was defined as M=128 kA/m, which was experimentally measured for samples of PDMS+NdFeB (20 vol %) composite. For the mechanical property of the softer segment, which is composed of the ferromagnetic elastomer composite only, the shear modulus value (G=455.6 kPa) measured for PDMS+ NdFeB (20 vol %) was used. Under the assumption of incompressible solids, for which E=3G, this shear modulus value is translated to Young's modulus of 1366.8 kPa. For the stiffer segment, which contains a 80-µm nitinol wire, the effective Young's modulus ($E_{eff}$=14008 kPa) was calculated from the following relation:

$$E_{eff} = \left( E_{core}\left(\frac{d}{D}\right)^4 + E_{jacket}\left(1 - \left(\frac{d}{D}\right)^4\right) \right) \quad (5)$$

where $E_{core}$ and $E_{jacket}$ denote the Young's moduli of the nitinol core and the ferromagnetic soft polymer jacket, respectively, while d and D denote the core and jacket diameter. For the nitinol core, Young's modulus of the martensite phase (40 GPa) was used for the calculation. This calculation was validated by the good agreement between the simulation and experimental results presented in FIG. 20E.

Experimental Validation of Simulation Results

For experimental validation of the model-based simulation results presented in FIG. 20E, deflection angles were measured from circular beam specimens (diameter of 600 µm) with different aspect ratios (L/D=10, 15, 20) under uniform magnetic fields ranging from 5 to 60 mT generated by a pair of Helmholtz coils (10-cm diameter; MicroMagnetics). For each specimen, a nitinol core (diameter of 80 µm) was incorporated in the ferromagnetic soft polymer jacket based on PDMS+NdFeB (20 vol %) through the injection molding process described earlier to provide sufficient mechanical stiffness required to prevent gravitational sagging during the measurement. The incorporation of the stiff core results in ten-fold increase in the Young's modulus (and therefore the bending stiffness as well) by 10 times as described above.

Magnetic Actuation and Demonstration

For all demonstrations presented herein, unless otherwise noted, a cylindrical NdFeB magnet (diameter and height of 50 mm; DY0Y0-N52, K&J Magnetic, Inc.) was used to apply magnetic fields required for actuation at distance. For magnetic steering and navigation, the direction and strength of the applied magnetic fields were varied by manually manipulating the magnet to change its position and orientation while advancing the proximal end of the template guidewire connected to the demonstrated ferromagnetic soft continuum robot. Detailed dimension of the demonstration setups in FIGS. 8 and 9, such as the location, height, and tilting angle of the rings, is provided in FIG. 17.

Figure 11:
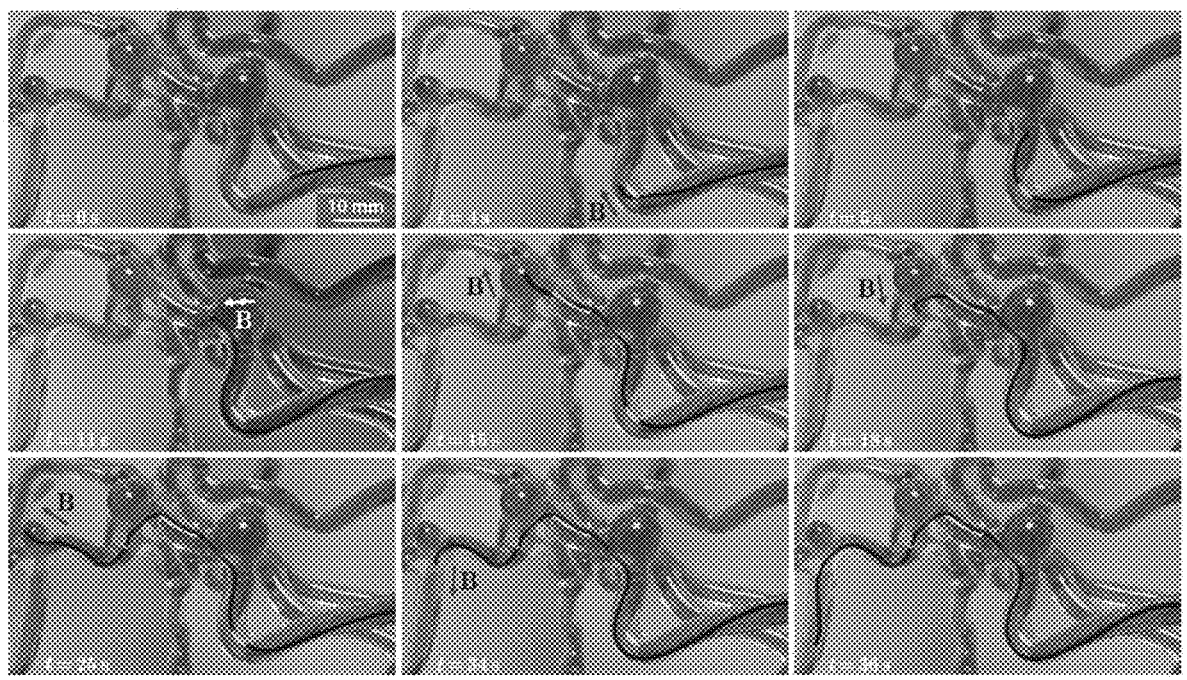
FIG. 11 illustrates a demonstration of navigating through a 3D neurovascular phantom network using a soft continuum robotic device according to an embodiment of the present invention, where the device first passes through the sharp corner with acute angulation (between t=0 s and t=5 s). The device makes another sharp turn after reaching the first aneurysm (t=11 s) based on the magnetic steering capability to reach the second aneurysm (t=15 s). Then, it makes another sharp turn at the acute-angled corner beneath the second aneurysm (t=18 s) to reach the third aneurysm (t=25 s), and navigates further downstream (t=36 s).

For demonstrations presented in FIGS. 11 and 12, a commercially available cerebrovascular phantom model made of silicone (Trandomed 3D) was used along with a blood-mimicking fluid (Replicator Fluid, Vascular Simulations Inc.), which simulates the friction between commercial hydrophilic guidewire/catheter surfaces and the real blood vessels when used with a silicone vascular model. Further details on the cerebrovascular phantom model is provided in FIG. 20. In these set of demonstrations, the steering and navigating tasks were controlled with visual feedback by manually manipulating the position and orientation of a single permanent magnet while advancing the whole body by pushing the proximal end. The magnetic manipulation under spatially non-uniform fields exploited the magnetic body torques as the main source of actuation as well as the magnetic body forces, which further help the robot's tip to align itself towards the desired direction more effectively (more detailed discussions on the actuation mechanisms are available in Supplementary Text). For steerable laser delivery demonstration presented in FIGS. 6 and 12, a 3,100-mW green LED (530-nm wavelength; Thorlabs Inc.) was used as a light source.

Optimization Design

Both magnetic and mechanical properties of the robot's body made of ferromagnetic soft composites vary with the particle loading concentration. A material design strategy is described here to optimize the actuation performance of the present invention ferromagnetic soft continuum robotic device. Based on the theoretical framework developed for ferromagnetic soft materials (Y. Kim, H. Yuk, R. Zhao, S. A. Chester, X. Zhao, *Printing ferromagnetic domains for untethered fast-transforming soft materials*, Nature 558, 274-279 (2018); R. Zhao, Y. Kim, S. A. Chester, P. Sharma, X. Zhao, *Mechanics of hard-magnetic soft material*, J. Mech. Phys. Solids 124, 244-263 (2019).), we first provide the fundamental equations for quantitative description of the deformation of ferromagnetic soft materials upon magnetic actuation. The magnetic moment density (or magnetization) at any point of a ferromagnetic soft material in the reference (undeformed) configuration is denoted by a vector M. Under an applied magnetic field, denoted by a vector B, the ferromagnetic soft material can deform. The deformation at any point of the material is characterized by the deformation gradient tensor F. The application of the magnetic field on the embedded magnetic moment in the material generates the magnetic Cauchy stress that drives $\sigma^{magnetic}=B \otimes FM$ the deformation, where the operation $\otimes$ denotes the dyadic product which takes two vectors to yield a second order tensor. Meanwhile, the deformation of the material generates the elastic Cauchy stress $\sigma^{elastic}$, which is also a function of F defined by hyperelastic constitutive models such as the neo-Hookean model. The total Cauchy stress in the material $\sigma=\sigma^{elastic}+\sigma^{magnetic}$ is then substituted into the equilibrium equation in Eq. (S3) (See Supplementary Text), from which the deformation (i.e. F) can be evaluated at every material point in equilibrium. While alternate approaches based on magnetic body forces and torques have been proposed to calculate the deformation of ferromagnetic soft materials, the current approach based on the magnetic stress can be readily implemented in commercial finite-element software packages such as Abaqus. In addition, the magnetic stress can readily recover the magnetic body force and torque densities used in other approaches (see Supplementary Text for details).

Figure 16A:
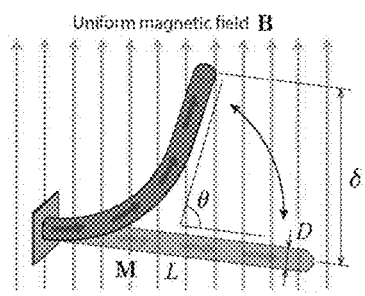
FIGS. 16A-I illustrate an example of optimizing the design of the ferromagnetic soft continuum robotic device according to embodiments of the present invention, with FIG. 16A showing a schematic of the device with uniform magnetization M along the axial direction deflecting towards the direction of the uniform magnetic field B applied perpendicularly to the body (the unconstrained length and the outer diameter of the robot are denoted L and D, respectively. δ indicates the deflection of the free end, and θ indicates the deflection angle), FIG. 16B graphically illustrates the magnitude of magnetization (denoted M) linearly varying with the volume fraction of the embedded magnetic particles, FIG. 16C graphically illustrates the shear modulus (denoted G) of the ferromagnetic composite at different particle concentrations, FIG. 16D graphically illustrates a prediction of the variation of M/G, a characteristic quantity that determines the degree of deflection for small bending, with the particle volume fraction under given applied field strength for a given geometry (the unit of this quantity, $T^{-1}$, or equivalently Am/N, is intentionally omitted for simplicity), FIG. 16E graphically illustrates the actuation angle predicted from finite element simulation and experimental measurements plotted against the applied field strength normalized by material properties (M and G) for a particular composition (20 vol %) with different aspect ratios: L/D=10, 15, 20, FIG. 16F graphically illustrates the variation of actuation angle with particle concentration at different actuation field strengths: B=10, 20, 40, 80 mT, predicted from simulation results when L/D=10, FIG. 16G graphically illustrates predictions of the variation of $M^2/G$, a quantity that characterizes the energy density in a deflected body for small bending case, with the particle volume fraction under given applied field strength for a given geometry. The unit of this quantity, $A^2/N$, is intentionally omitted for brevity, and FIGS. 16H-I graphically depict the average energy density predicted by finite element simulations for small (FIG. 16H) and large (FIG. 16I) bending cases, as a function of particle concentration.
Figure 16B:
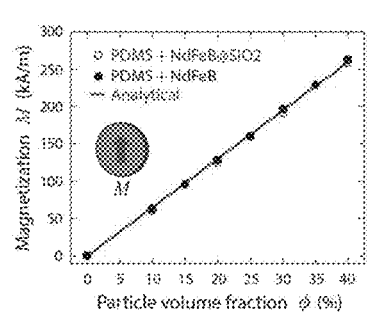

Since the magnetically responsive tip of the present invention soft continuum robotic device is axially magnetized (i.e. M along the axial direction), the tip tends to bend along the applied magnetic field B (FIG. 5B) due to the magnetic body torques generated from the embedded magnetized particles. To find the optimal particle concentration that yields the largest bending under given conditions and geometry, without loss of generality, we consider a beam of length L and diameter D under uniform magnetic field B that is being applied perpendicularly to M (FIG. 16A). Also, to utilize a tractable analytical solution, we further assume that the magnetically active tip undergoes small bending, where the deflection (denoted in FIG. 16A) is below 10% of the tip length L. Then, we can reach the following analytical expression for the deflection of the magnetically active tip (details are available in Supplementary Text):

$$\frac{\delta}{L} = \frac{16}{9}\left(\frac{MB}{G}\right)\left(\frac{L}{D}\right)^2 \qquad (1)$$

where M and B are the magnitudes of the magnetization and the applied magnetic field, respectively, and G denotes the shear modulus of the material, which is considered as a neo-Hookean solid in the current analysis. Eq. (1) relates the material properties (magnetization M and shear modulus G), geometry (beam length L and diameter D), and actuating field strength B to the normalized deflection. From Eq. (1), it can be deducted that for small bending, the deflection of the beam is linearly proportional to a dimensionless quantity MB/G while quadratically dependent on the aspect ratio L/D. The dimensionless quantity MB/G can be interpreted as the actuating field strength normalized by the material properties. Given that both M and G are dependent on the particle volume fraction, Eq. (1) implies that there will likely be an optimal point at which the normalized deflection is maximized.

Figure 16C:
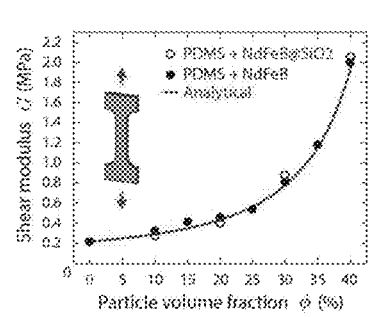

The magnetization of the ferromagnetic soft composite is linearly proportional to the volume fraction of NdFeB particles (FIG. 16B), and hence can be expressed as $$M = M_p \phi \qquad (2)$$

where $M_p$ denotes the magnetization of the magnetic particles, and $\phi$ denotes the particle volume fraction. Unlike the magnetization, the shear modulus increases nonlinearly as the particle concentration increases (FIG. 16C). This nonlinear dependence of shear modulus can be predicted by a simple analytical expression in Eq. (3), so-called a Mooney model, under the assumption that the increase in the shear modulus of particle-filled elastomer composites is analogous to the increase in the viscosity of particle suspensions.

$$G = G_o \exp\left(\frac{2.5\phi}{1-1.35\phi}\right) \qquad (3)$$

where $G_o$ denotes the shear modulus of a pure elastomer with no particle. No significant difference is observed in both magnetization (FIG. 16B) and shear modulus (FIG. 16C) between the composite based on uncoated particles (PDMS+NdFeB) and the composite based on silica-coated particles (PDMS+NdFeB@SiO$_2$), which may be attributed to the marginal change in the particle volume due to the marginal thickness of the silica shell as discussed earlier. The small difference in shear modulus between the two types of composites also implies that the affinities of silicone elastomers with metal oxide (of uncoated particles) and silicon oxide (of silica-coated particles) surfaces are not substantially different.

Figure 16D:
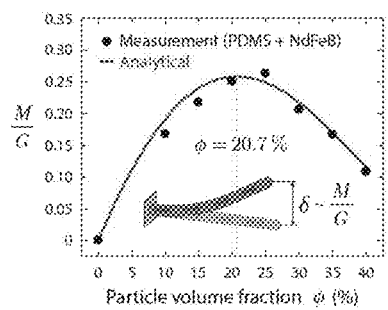
Figure 16F:
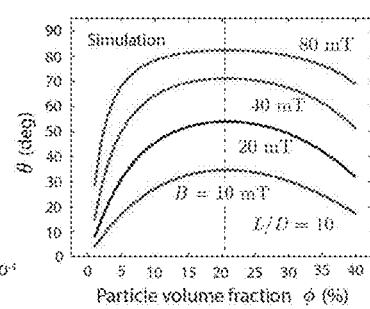

By substituting Eqs. (2) and (3) into Eq. (1), the critical concentration at which the deflection is maximized for given conditions (field strength B and the geometric factor L/D) can be identified. The critical volume fraction is calculated to be 0.207 (or 20.7 vol %), independent of $M_p$ and $G_o$ (FIG. 16D). It should be noted that this critical concentration is obtained for small bending scenarios as described above. For large bending, the simulation and experimental results in FIG. 16E indicate that the actuation angle (defined in FIG. 16A) monotonically increases as a function of the normalized field strength MB/G for different aspect ratios L/D. Therefore, it is anticipated that the critical concentration predicted from the small-deflection analysis will remain effective for large bending cases as well. This is further validated by the simulation results for large bending presented in FIG. 16F, which show the actuation angle varying with the material composition and the applied field strength for a fixed geometry. The results clearly indicate that the actuation angle reaches its maximum, for given applied field strengths, at the critical volume fraction (20.7 vol %) predicted above for small bending case. As the applied field strength increases, however, the actuation angle begins to saturate while approaching 90 degrees, making the curves around the peak flat (FIG. 16F).

When producing mechanical work out of magnetic actuation is of greater importance than the large deflection, the actuation performance can be optimized in terms of the energy density, which corresponds to the amount of work (per unit volume) one can extract from the continuum robotic device. For small bending, the equivalent force generated at the free end of the beam can be calculated as F=MBA (see Supplementary Text), where A denotes the cross-sectional area of the beam. Combining this with Eq. (1), an analytical expression for the energy density u is as follows:

$$u = \frac{16}{9}\left(\frac{M^2 B^2}{G}\right)\left(\frac{L}{D}\right)^2 \tag{4}$$

Figure 16G:
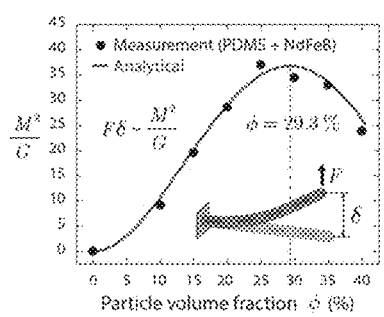
Figure 16H:
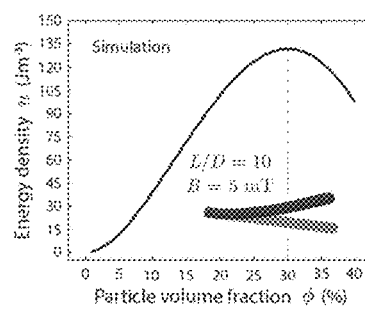
Figure 16I:
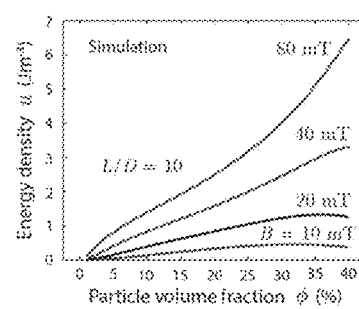

By substituting Eqs. (2) and (3) into Eq. (4), it can be deducted that the energy density reaches its maximum when the particle volume fraction is 29.3 vol % under given conditions in terms of applied field strength B and geometry L/D (FIG. 16G). This analytical prediction is validated by our model-based simulation for small bending (FIG. 16H), which shows how the energy density varies with the particle volume fraction when B=5 mT and L/D=10. As the bending becomes larger, however, the peak at which the energy density is maximized shifts to the right, towards the higher volume fractions (FIG. 16I). The peak eventually disappears when the actuation angle saturates, after which the energy density keeps increasing with the particle volume fraction. Qualitatively, this can be understood by considering the exponentially increasing stiffness (FIG. 16C), which dominantly contributes to the energy density when the deformation level remains almost unchanged (FIG. 16F).

When the material properties M and G are fixed due to a given particle volume fraction, the actuation performance of the present invention ferromagnetic soft continuum robotic device under given applied field strength can still be optimized by adjusting the aspect ratio, according to Eqs. (1) and (4) along with the simulation results presented in FIG. 16. This implies that fine features with high aspect ratios, such as cilia-like soft continuum robots, would require significantly lower field strength to induce the bending actuation. Given that a printing-based method can easily produce very fine features, down to 80 μm in terms of diameter, such extremely thin, cilia-like soft continuum robots may also be designed for applications that require manipulating highly delicate structures.

Supplementary Text

Analytical Model for Ferromagnetic Soft Continuum Robots

We denote the magnetic moment density (or magnetization) at any point of a ferromagnetic soft material in the undeformed, reference configuration by a vector M. Under an applied magnetic field, denoted by a vector B, the ferromagnetic soft material deforms (FIG. 16A). The deformation at any point of the material is characterized by the deformation gradient tensor F. The application of the magnetic field on the embedded magnetic moment in the material generates the magnetic Cauchy stress that drives its deformation. Meanwhile, the deformation of the material generates the elastic Cauchy stress. For incompressible solids, the magnetic Cauchy stress can be expressed as $$\sigma^{magnetic} = -B \otimes FM, \tag{S1}$$

where the operator $\otimes$ denotes the dyadic product, which takes two vectors to yield a second-order tensor. If adopting the incompressible neo-Hookean model among existing hyperelastic constitutive models, the elastic Cauchy stress $\sigma^{elastic}$ can be expressed as $$\sigma^{elastic} = GFF^T - p1, \tag{S2}$$

where G is the shear modulus, $F^T$ is the transpose of F, 1 is the identity tensor, and p is the hydrostatic pressure that needs to be determined from boundary conditions. Assuming a quasi-static process where the inertial effects are negligible, the total Cauchy stress $\sigma = (\sigma^{elastic} + \sigma^{magnetic})$ can then be substituted into the following equilibrium equation:

$$\text{div } \sigma b = 0, \tag{S3}$$

where div denotes the divergence, and b denotes the body force (e.g., gravitational) per unit volume. This equilibrium equation can be solved to calculate the deformation gradient F, thereby finding the equilibrium configuration of the ferromagnetic soft material under magnetic actuation. While alternate approaches based on magnetic forces and torques have been developed to calculate the deformation of ferromagnetic soft materials, the current approach based on magnetic stress can be readily implemented in commercial finite-element software packages such as Abaqus.

For the magnetically responsive tip of the present invention ferromagnetic soft continuum robotic device, the gravitational body force can be neglected due to the considerably greater contribution from the magnetic stress. For small bending, where the deflection of the free end is below 10% of the length, i.e., ($\delta/L \leq 0.1$, a tractable analytical expression can be derived for quantitative prediction of the degree of deflection. When a uniform magnetic field B is applied perpendicularly to the magnetically responsive tip with magnetization M along the axial direction (FIG. 3A), the only non-zero, shear stress component of the magnetic Cauchy stress tensor in the reference (undeformed) configuration (i.e., F=1) can be calculated from eq. S1 to be $\sigma^{magnetic} = -MB$ as a scalar quantity. This shear stress gives rise to magnetic moment T=−MBAL across the body, where A denotes the cross-sectional area (A=$\pi D^2/4$) of the circular beam of length L and diameter D. Equivalently, this magnetic moment can be considered to be generating a point force F=MBA at the free end of the beam along the applied field direction (as illustrated in the schematic in FIG. 6G). The bending stiffness of a beam can be expressed as $K_b = 3EI/L^3$, where E denotes the Young's modulus of the constituent material, and I denotes the area moment of inertia, which can be expressed as $I=\pi D^4/64$ for a circular beam of diameter D. Then, the deflection of the free end of the beam, denoted $\delta$, under this point force can be analytically expressed for small deflection case as $$\delta = \frac{F}{K_b} = \frac{16MBL^3}{3ED^2}. \tag{S4}$$

For incompressible solids, for which $E=3G$, eq. S4 can be expressed in a normalized from as $$\frac{\delta}{L} = \frac{16}{9}\left(\frac{MB}{G}\right)\left(\frac{L}{D}\right)^2, \tag{S5}$$

which is identical to Eq. 1 introduced in the main text. From this analytical expression, it becomes evident that the normalized deflection of the magnetically responsive tip of the ferromagnetic soft continuum robot under magnetic actuation is determined by the two dimensionless factors: MB/G and L/D. The former can be interpreted as the applied field strength B normalized by the material properties M and G, while the latter is the aspect ratio, a geometric factor that can largely affect the bending stiffness of the beam. Also, the work done by the equivalent point force F while deforming the beam by small deflection $\delta$, can be expressed as $$W = F\delta = \frac{4\pi}{9}\left(\frac{M^2B^2}{G}\right)L^3. \tag{S6}$$

When divided by the volume, eq. S6 leads to the following expression for the energy density:

$$u = \frac{16}{9}\left(\frac{M^2B^2}{G}\right)\left(\frac{L}{D}\right)^2, \tag{S7}$$

which is identical to Eq. 4 introduced in the main text. Here, it is assumed that no energy is dissipated during the deformation, based on the underlying assumption of hyperelastic solids.

Alternative Model Based on Magnetic Body Force and Torque

As discussed in the previous section, the current model for ferromagnetic soft materials is based on the magnetic Cauchy stress and the total Cauchy stress. Since the traditional approaches are commonly based on the magnetic body force and torque and the elastic Cauchy stress, here we describe how the magnetic Cauchy stress presented in eq. S1 is elated to the magnetic body force and torque in the following paragraphs.

Under the assumption of ideal hard-magnetic soft materials, which holds for the present invention ferromagnetic soft continuum robotic device, the magnetization vector M can be considered independent of the externally applied magnetic field B, provided that the materials are magnetically saturated and that the applied field strength is far below the coercivity, at which the reversal of remnant magnetization takes place.

For an incompressible ideal hard-magnetic soft material, the magnetic body torque per unit volume of the material (i.e., magnetic body torque density) generated by the external field B applied to the magnetization M can be expressed as a consequence of the angular momentum balance as $$\tau^{magnetic}=-\varepsilon:(\sigma^{magnetic})^T=FM\times B, \tag{S8}$$

where $\varepsilon=\varepsilon_{ijk}e_i\otimes e_j\otimes e_k$ is the third-order permutation tensor; the operator : denotes the double contraction of two tensors; and FM accounts for the reoriented magnetization vector in the current (deformed) configuration. Also, the magnetic body force acting on the material per unit volume (i.e., magnetic body force density) under the applied magnetic field B can be expressed from eqs. S1 and S3 as $$b^{magnetic}=-\mathrm{div}\,\sigma^{magnetic}=(\mathrm{grad}B)FM, \tag{S9}$$

where gradB denotes the spatial gradient of the applied magnetic field, which gives rise to the magnetic body force. Again, FM represents the reoriented magnetization vector in the current (deformed) configuration. Note that the magnetic body torque and force densities in eqs. S8 and S9 are consistent with their common expressions used elsewhere in the literature.

As shown above, our approach based on the magnetic Cauchy stress enables the magnetic body torques and forces to be treated as stresses when solving the equilibrium equations to find the final configuration of the ferromagnetic soft continuum robotic devices under external magnetic fields. When the magnetic body torque and force (instead of the magnetic Cauchy stress) are directly employed to calculate the deformation, the elastic Cauchy stress (instead of the total Cauchy stress) can be used in the equilibrium equations. While the models based on the magnetic Cauchy stress or the magnetic body torque and force will reach the same deformation, the current approach based on the magnetic Cauchy stress can be readily implemented in commercial finite-element software packages such as Abaqus and hence enables accurate and quantitative prediction of the final configuration of the robot under given conditions and geometries.

Magnetic Actuation and Steering with a Cylindrical Permanent Magnet

For the demonstrations presented earlier, a cylindrical NdFeB magnet (DY0Y0-N52, K&J Magnetic, Inc.) was employed to demonstrate the magnetic steering function of the proposed ferromagnetic soft continuum robot. The radius (25 mm) and height (50 mm) of the cylindrical magnet are denoted as R and H, respectively (FIG. 18A). The basic principle behind the magnetic steering is to align the central axis of the magnet along a desired direction to induce the bending actuation on the robot's magnetically responsive tip towards and along the desired direction (FIG. 18B). The degree of bending, which is determined by the applied field strength, is controlled by adjusting the distance between the magnet and the robot. The magnetic field strength along the central axis of the magnet can be expressed as a function of distance from the surface (denoted z in FIG. 18A) as $$B_z(0,0,z) = \frac{B_0\sqrt{R^2+H^2}}{H}\left(\frac{z+H}{\sqrt{(z+H)^2+R^2}}-\frac{z}{\sqrt{z^2+R^2}}\right), \tag{S10}$$

where $B_0$ denotes the surface field strength, which is 662 mT for the specific magnet used. Typical working distance for the set of demonstrations presented earlier ranges from around 40 to 80 mm, which corresponds to the field strength ranging from around 20 to 80 mT, according to eq. S10. As discussed earlier, under spatially uniform magnetic fields, the bending actuation of the ferromagnetic soft continuum robot is driven by magnetic body torques generated from the embedded magnetic particles. However, when the applied actuating field is spatially nonuniform, which is the case when a single permanent magnet is used for actuation, magnetic body force does exist and can contribute to the magnetic steering and control of the robot.

Influence of a FieldGgradient on the Magnetic Actuation and Steering

Figure 19:
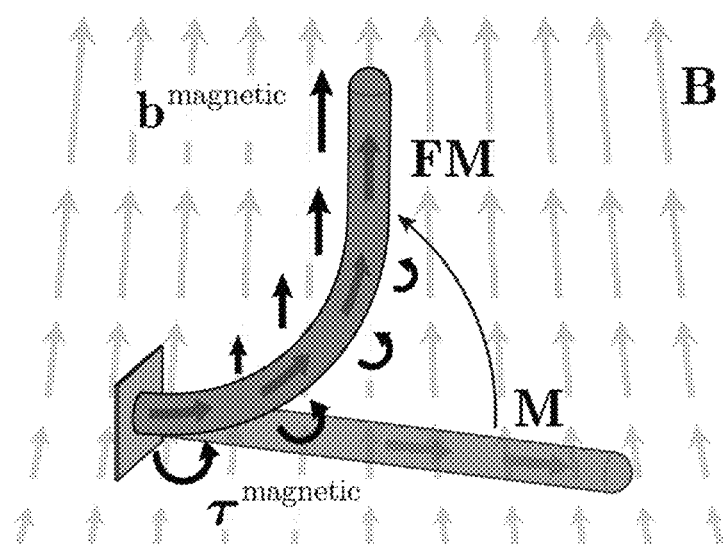
FIG. 19 shows influence of spatial gradients of the actuating magnetic field on the actuation and steering of the ferromagnetic soft continuum robot according to an embodiment of the present invention, where the magnetic field B generated along the central axis of a large cylindrical magnet is applied perpendicularly to the magnetization vector M along the body, which gives rise to magnetic body torques ($\tau^{magnetic}$) that drive the bending actuation. As the body deforms under the applied field with spatial gradients along the field direction, magnetic body forces ($b^{magnetic}$) are generated. As the magnetization in the current configuration FM becomes more aligned with the applied field direction, the magnetic body force increases whereas the magnetic body torque decreases. This means that, when the robotic device is actuated and controlled with a magnet, the bending actuation is initiated and driven by the magnetic body torque and then further supported by the magnetic body force as the robot's elongate body deforms.

When the magnet used for actuation is sufficiently larger than the responsive segment of the robot being actuated, we may neglect the nonlinear edge effects and further assume that the magnetic fields are almost parallel and that their spatial gradients are dominant along the central axis (z-direction) in terms of the magnitude, as illustrated in FIG. 19. Then, the field gradient along the central axis of the cylindrical magnet discussed above can be obtained from eq. S10 as $$\frac{\partial B_z}{\partial z} = \frac{B_0 \sqrt{R^2 + H^2}}{H} \left( \frac{1}{\sqrt{(z+H)^2 + R^2}} - \frac{1}{\sqrt{z^2 + R^2}} + \frac{z^2}{(z^2 + R^2)^{3/2}} - \frac{(z+H)^2}{((z+H)^2 + R^2)^{3/2}} \right). \tag{S11}$$

This gives the gradient values ranging from around 0.5 to 4 mT/mm over the range of typical working distance (40 to 80 mm) mentioned above. Under this range of field gradients, the magnetic body force per unit volume can be estimated from eq. S9 to be on the order of 64 to 512 kN/m$^3$, when assuming that the robot's tip is aligned with the central axis of the magnet as illustrated in FIG. 19. Compared to this, the gravitational body force per unit volume is calculated to be on the order of 23 kN/m$^3$ for ferromagnetic soft composite based on PDMS+NdFeB (20 vol %), whose mass density is 2.273 g/cm$^3$. This means that the field gradient along the central axis of the magnet is generating sufficient magnetic body forces in the deformed configuration to maintain the robot's deflected tip, as illustrated in FIG. 19.

As eq. S9 implies, however, the magnetic body force varies with the configuration, or more specifically, the alignment between the robot's magnetization and the external field. In the reference configuration in FIG. 19, in which the external field is being applied perpendicularly to the magnetization vector, the magnetic body force acting along the magnet's central axis is considered to be almost negligible. As the body deforms and the robot's magnetization becomes more aligned with the central axis of the magnet, the magnetic body force increases. Therefore, we can conclude that, when the robot is actuated and controlled with a magnet, the bending actuation in general is initiated and driven by the magnetic body torque and then facilitated and further supported by the magnetic body force as the robot's elongate body deforms. We therefore can also conclude that utilizing spatial gradients to exploit magnetic body forces for bending actuation can be a good strategy to more effectively control the robot's configurations, as demonstrated in the series of functional tasks presented earlier.

What is claimed is:

1. A continuum robotic device for use in minimally invasive procedures comprising:

an elongate body having a proximal end, a distal end, an inner core and an outer shell;
the outer shell fabricated of an elastomer;
a plurality of ferromagnetic microparticles dispersed within the outer shell;
the elongate body having an initial shape;
wherein the elongate body has an outer diameter of less than 1000 µm, and wherein exposure of the device to an external magnetic field magnetically activates the plurality of ferromagnetic microparticles to provide the elongate body in an activated shape different than the initial shape.

2. The device of claim 1, wherein exposure of the device to an external magnetic field magnetically activates the plurality of ferromagnetic microparticles to provide omnidirectional steering of the device.

3. The device of claim 1, wherein the plurality of ferromagnetic microparticles are uniformly magnetized along an axial direction of the elongate body.

4. The device of claim 1, wherein the plurality of ferromagnetic microparticles are magnetized in nonuniform patterns of magnetic polarity along an axial direction of the elongate body.

5. The device of claim 1, wherein the plurality of ferromagnetic microparticles are magnetized in patterns of magnetic polarity comprising alternating patterns of different magnetic polarities.

6. The device of claim 5, wherein alternating patterns of different magnetic polarities are disposed such that exposure of the device to an external magnetic field magnetically activates the plurality of ferromagnetic microparticles to provide the elongate body in a wavy shape.

7. The device of claim 1, wherein the inner core and outer shell and fabricated, and the plurality of ferromagnetic microparticles are dispersed, such that exposure of the device to various direction and magnitudes of external magnetic fields provides the body in a variety of activated shapes different than the initial shape.

8. The device of claim 1, wherein the elongate body has an outer diameter no greater than 900 µm.

9. The device of claim 1, further comprising a hydrogel skin disposed on the outer shell.

10. The device of claim 9, wherein the hydrogel skin has a thickness of 10 µm to 25 µm.

11. The device of claim 1, wherein the ferromagnetic microparticles have an average particle size of 2 µm to 10 µm.

12. The device of claim 1, wherein the inner core is a metallic wire.

13. The device of claim 12, wherein the metallic wire is fabricated of superelastic nickel-titanium, stainless steel, platinum a platinum-tungsten alloy, a cobalt-chromium-molybdenum alloy, or combinations thereof.

14. The device of claim 1, wherein the inner core comprises one or more optical fibers.

15. The device of claim 1, wherein the elongate body further includes one or more imaging, illumination, laser delivery, or sensing elements at or near the distal end.

16. The device of claim 14, wherein the inner core is a fiber optic shape sensor.

17. The device of claim 16, wherein the fiber optic shape sensor comprises one or more Bragg grating.

18. The device of claim 1, wherein the outer shell is fabricated of one or more polymer materials having a Young's modulus below 20 MPa.

19. The device of claim 18, wherein the outer shell is fabricated of an elastomer.

20. The device of claim 18, herein the outer shell is fabricated of one or more materials selected from natural rubbers, synthetic rubbers, and thermoplastic elastomers.

21. The device of claim 20, wherein the outer shell is fabricated of one or more materials selected from silicone rubber, polyacrylate rubber, thermoplastic polyurethane, and styrene-ethylene-butylene-styrene (SEBS).

22. The device of claim 1, wherein the plurality of ferromagnetic microparticles are selected from neodymium iron boron (NdFeB), samarium cobalt (SmCo), aluminum-nickel-cobalt (AlNiCo), copper-nickel-iron (CuNiFe), barium-iron oxide (BaFeO), platinum-cobalt alloys, and combinations thereof.

23. The device of claim 1, wherein the ferromagnetic microparticles have programmed magnetic polarities that enable magnetic actuation upon exposure to an external magnetic field.

24. The device of claim 1, wherein the plurality of ferromagnetic microparticles are coated with a non-corrosive layer.

25. The device of claim 24, wherein the non-corrosive layer is fabricated of one or more materials selected from silica, Parylene C, gold, and epoxies.

26. The device of claim 1, wherein the inner core extends through a portion of the elongate body that is less than an entire length of the elongate body.

27. The device of claim 26, wherein a portion of the elongate body at the distal end does not include the inner core.

28. The device of claim 1, wherein the inner core tapers in diameter towards the distal end of the elongate body.

29. The device of claim 1, wherein the elongate body comprises one or more magnetically active portions comprising one or more outer shell portions containing a plurality of ferromagnetic particles dispersed therein, and one or more inactive portions comprising one or more one or more outer shell portions not containing a plurality of ferromagnetic particles dispersed therein.

30. The device of claim 29, wherein a distal end portion of the elongate body comprises a distal magnetically active portion, and an adjacent portion of the elongate body proximal the distal magnetically active portion comprises a magnetically inactive portion.

31. A method of performing a minimally invasive procedures on the microvascular system comprising:
providing a continuum robotic device comprising an elongate body having a proximal end and a distal end, the elongate body including an inner core and an outer shell; the outer shell fabricated of an elastomer; a plurality of ferromagnetic microparticles dispersed within the outer shell; and the elongate body having an initial shape, wherein the elongate body has an outer diameter of less than 1000 μm;
inserting the distal end into a blood vessel connected to one or more target sites of the microvascular system; and
actively guiding the distal end and advancing the elongate body through the microvascular system, including non-linear branches of the microvascular system, to the one or more target sites using an external magnetic field to activate the plurality of ferromagnetic microparticles, wherein the external magnetic field is selectively applied to the elongate body,
wherein selectively exposing the elongate body to one or more external magnetic fields is carried out so as to provide the elongate body in a variety of activated shapes configured to guide the distal end and advance the elongate body through microvascular system to the one or more target sites.

32. The method of claim 31, wherein selectively exposing the elongate body to one or more external magnetic fields creates multiple controllable modes and degrees of bending of the elongate body depending on a direction and strength of the external magnetic field.

33. The method of claim 31, wherein a user performs the method remotely by viewing the device within the microvascular system using real time imaging, and applying the one or more external magnetic fields using a robotic manipulation platform.

34. The method of claim 31, wherein the minimally invasive procedure is a cerebrovascular or endovascular procedures.

35. The method of claim 31, wherein the one or more target sites are selected from one or more aneurysms, embolisms, lesions, or arteries.

36. The method of claim 31, wherein the device inner core comprises one or more optical fiber, and the device further includes a laser delivery element at the distal end, and the method further comprises guiding and advancing the distal end to one or more target sites selected from vascular occlusions, atherosclerosis, aneurysms, embolisms, and lesions, and treating the one or more target sites with the laser.

37. The method of claim 31, wherein the device inner core comprises one or more optical fiber, and the device further includes one or more imaging, sensing, and/or illumination elements, and the method further comprises providing imaging, sensing, and/or illumination while guiding the distal end and advancing the elongate body through the microvascular system to the one or more target sites.

38. The method of claim 31, wherein the device inner core comprises one or more fiber optic shape sensors, and the method further comprises using the one or more fiber optic shape sensors to provide a user with real-time feedback of a 3D shape of the elongate body.

39. The method of claim 38, wherein the one or more fiber optic shape sensors comprise one or more Bragg grating, and the method further comprises exposing the one or more Bragg grating to strain or temperature to shift a wavelength of the Bragg grating, and determining a direction and magnitude of the shift.

40. A system for performing a minimally invasive procedures on the microvascular system comprising:
a continuum robotic device for use in minimally invasive procedures comprising: an elongate body having a proximal end, a distal end, an inner core and an outer shell; the outer shell fabricated of an elastomer; a plurality of ferromagnetic microparticles dispersed within the outer shell; the elongate body having an initial shape; wherein the elongate body has an outer diameter of less than 1000 μm; and
a control mechanism comprising a single permanent magnet held and manipulated by a multi-degree of freedom (DOF) robotic arm,
wherein exposure of the continuum robotic device to an external magnetic field from the control mechanism magnetically activates the plurality of ferromagnetic microparticles to provide the elongate body in an activated shape different than the initial shape.

* * * * *